US012692286B2

(12) United States Patent
Koch et al.

(10) Patent No.: US 12,692,286 B2
(45) Date of Patent: Jul. 28, 2026

(54) CRYSTALLIZATION OF ALLULOSE UNDER REDUCED PRESSURE

(71) Applicant: SAVANNA INGREDIENTS GMBH, Elsdorf (DE)

(72) Inventors: Timo Johannes Koch, Elsdorf (DE); Stephan Mohr, Eushkirchen (DE)

(73) Assignee: SAVANNA INGREDIENTS GMBH, Elsdorf (DE)

( * ) Notice: Subject to any disclaimer, the term of this patent is extended or adjusted under 35 U.S.C. 154(b) by 879 days.

(21) Appl. No.: 17/917,888

(22) PCT Filed: May 26, 2021

(86) PCT No.: PCT/EP2021/064055
§ 371 (c)(1),
(2) Date: Oct. 7, 2022

(87) PCT Pub. No.: WO2021/239813
PCT Pub. Date: Dec. 2, 2021

(65) Prior Publication Data
US 2023/0159579 A1 May 25, 2023

(30) Foreign Application Priority Data

May 27, 2020 (EP) ..................................... 20176791
Nov. 10, 2020 (EP) ..................................... 20206593

(51) Int. Cl.
| | |
|---|---|
| *C07H 1/06* | (2006.01) |
| *C07H 3/02* | (2006.01) |
| *C30B 7/04* | (2006.01) |

(52) U.S. Cl.
CPC ................. *C07H 1/06* (2013.01); *C07H 3/02* (2013.01); *C30B 7/04* (2013.01)

(58) Field of Classification Search
CPC ................. C07H 1/06; C07H 3/02; C30B 7/04
See application file for complete search history.

(56) References Cited

U.S. PATENT DOCUMENTS

| | | | |
|---|---|---|---|
| 3,880,593 | A | 4/1975 | Windal |
| 4,357,172 | A | 11/1982 | Edwards |
| 5,411,880 | A | 5/1995 | Izumori et al. |
| 8,030,035 | B2 | 10/2011 | Oh et al. |
| 8,735,106 | B2 | 5/2014 | Hong et al. |
| 2011/0237790 | A1 | 9/2011 | Lee et al. |
| 2014/0342044 | A1 | 11/2014 | Bell et al. |
| 2014/0370171 | A1 | 12/2014 | Takaoka et al. |
| 2015/0210996 | A1 | 7/2015 | Woodyer et al. |
| 2016/0050954 | A1 | 2/2016 | Barre et al. |
| 2016/0302463 | A1 | 10/2016 | Woodyer et al. |
| 2017/0064988 | A1 | 3/2017 | Prakash et al. |
| 2017/0313734 | A1 | 11/2017 | Kim et al. |
| 2018/0049458 | A1 | 2/2018 | Woodyer et al. |
| 2018/0255814 | A1 | 9/2018 | Park et al. |
| 2018/0271112 | A1 | 9/2018 | Barkalow et al. |
| 2018/0271113 | A1 | 9/2018 | Parady et al. |
| 2018/0279643 | A1 | 10/2018 | Barkalow et al. |
| 2018/0281263 | A1 | 10/2018 | Rust |
| 2018/0327796 | A1 | 11/2018 | Lee et al. |
| 2019/0029299 | A1 | 1/2019 | Bak et al. |
| 2019/0090528 | A1 | 3/2019 | Boit et al. |
| 2019/0232720 | A1 | 8/2019 | Prost et al. |
| 2019/0246673 | A1 | 8/2019 | Park et al. |
| 2019/0297931 | A1 | 10/2019 | Koch et al. |
| 2019/0330253 | A1 | 10/2019 | Boit et al. |
| 2020/0001502 | A1 | 1/2020 | Rust |
| 2020/0040023 | A1 | 2/2020 | Iyer et al. |
| 2020/0062792 | A1 | 2/2020 | Dou et al. |
| 2020/0085090 | A1 | 3/2020 | Boit et al. |
| 2020/0196648 | A1 | 6/2020 | Kim et al. |
| 2020/0385415 | A1 | 12/2020 | Park et al. |
| 2021/0009619 | A1 | 1/2021 | Iyer et al. |

FOREIGN PATENT DOCUMENTS

| | | |
|---|---|---|
| CN | 101109021 A | 1/2008 |
| CN | 104447888 A | 3/2015 |
| CN | 107699557 A | 2/2016 |

(Continued)

OTHER PUBLICATIONS

A. Kwiecien et al., "Crystal Structure of β-D-psicopyranose", Carbohydrate Research, 343(13), 2008, 2336-2339.
K. Fukada et al., "Crystal Structure, Solubility, and Mutarotation of the Rare Monosaccharide D-Psicose", Bulletin of the Chemical Society of Japan, 2010, 83(10), 1193-1197.
J. Angyal et al., "The Composition of Reducing Sugars in Solution", Advances in Carbohydrate Chemistry, vol. 42, Academic Press, New York, 1984, 15-68.
R.N. Goldberg et al., "Thermodynamic and Transport Properties of Carbohydrates and their Monophophates: The Pentoses and Hexoses", Journal of Physical and Chemical Reference Data, vol. 18(2), 1989, 809-880, p. 827.

(Continued)

*Primary Examiner* — Jonathan S Lau
(74) *Attorney, Agent, or Firm* — The Dobrusin Law Firm, P.C.

(57) ABSTRACT

The invention relates to a process for the preparation of a solid allulose material comprising crystalline allulose, the method comprising the steps of (a) providing in an evaporating crystallizer an aqueous mother liquor containing dissolved allulose; (b) maintaining, preferably until the end of crystallization, the aqueous mother liquor within the evaporating crystallizer at a crystallization temperature within the range of from 20 to 80° C.; (c) maintaining, preferably until the end of crystallization, the vapor phase above the aqueous mother liquor within the evaporating crystallizer at a crystallization pressure within the range of from 40 to 500 mbar; and (d) inducing crystallization of allulose from the aqueous mother liquor at the crystallization temperature and at the crystallization pressure in a super-saturated state thereby obtaining the solid allulose material as a precipitate and a supernatant.

20 Claims, 5 Drawing Sheets

(56)     References Cited

FOREIGN PATENT DOCUMENTS

| CN | 106480125 A | 3/2017 |
|---|---|---|
| CN | 109306365 A | 2/2019 |
| CN | 110627847 A | 12/2019 |
| CN | 110 872 332 A | 3/2020 |
| DE | 2315835 B2 | 11/1977 |
| EP | 0919127 A1 | 6/1999 |
| EP | 2552241 A2 | 2/2013 |
| EP | 3553071 A1 | 10/2019 |
| GB | 2536304 A | 9/2016 |
| JP | H05277000 A | 10/1993 |
| JP | 2005006520 A | 1/2005 |
| KR | 20160062349 A | 6/2016 |
| KR | 2019/0003307 A | 1/2019 |
| WO | 2015/075473 A1 | 5/2015 |
| WO | 2016/012854 A1 | 1/2016 |
| WO | 2016/135358 A1 | 9/2016 |
| WO | 2016/135458 A1 | 9/2016 |
| WO | 2017/029244 A1 | 2/2017 |
| WO | 2018/087261 A1 | 5/2018 |
| WO | 2018/105931 A1 | 6/2018 |
| WO | 2018/149707 A1 | 8/2018 |
| WO | 2019/004554 A1 | 1/2019 |
| WO | 2019/082206 A1 | 5/2019 |
| WO | 2019/083069 A1 | 5/2019 |
| WO | 2019/088654 A1 | 5/2019 |
| WO | 2020/005021 A1 | 1/2020 |
| WO | 2021/160564 A1 | 8/2021 |
| WO | 2021/239813 A1 | 12/2021 |

OTHER PUBLICATIONS

American Society of Agricultural and Biological Engineers (ASABE), ANSI/ASAE S319.Feb. 4, 2008 "*Method of Determining and Expressing Fineness of Feed Materials by Sieving*".

Sugar Technology, Beet and Cane Sugar Manufacture, Peter van der Poel, Hubert Schiweck, Tom Schwartz, 1998. Chapters 12-14. (particularly chapter 14).

International Search Report and Written Opinion, PCT Application No. PCT/EP2021/064055 dated Jul. 20, 2021.

European Search Report, EP Application No. 20176791.0 dated Oct. 12, 2020.

H. Itoh, et al., "Preparation of D-Psicose from D-Fructose by Immobilized D-Tagatose 3-Epimerase", Journal of Fermentation Bioengineering, 80(1), pp. 101-103 (1995).

N. Wagner, et al., "Practical Aspects of Integrated Operation of Biotransformation and SMB Separation for Fine Chemical Synthesis", Organic Process Research Development, 16, pp. 323-330 (2012).

N. Wagner, et al., "Model-based cost optimization of a reaction-separation integrated process for the enzymatic production of rare sugar D-psicose at elevated temperatures", Chemical Engineering Science, 137, pp. 423-435 (2015).

N. Wagner, et al., "A Separation-Integrated Cascade Reaction to Overcome Thermodynamic Limitations in Rare-Sugar Synthesis", Angewandte Chemie [Applied Chemistry] Int. Ed. Engl. 54(14), pp. 4182-4186 (2015).

Bosshart, et al., "Highly Efficient Proeduction of Rare Sugars D-Psicose and L-Tagatose by Two Engineered D-Tagatose Epimerases", Biotechnology Bioengineering, 113(2), pp. 349-358 (2016).

N. Wagner, et al., "Multi-objective optimization for the economic production of D-psicose using simulated moving bed chromatography", Journal of Chromatography A, 1398, pp. 47-56, (2015).

CRYSTALLIZATION OF ALLULOSE UNDER REDUCED PRESSURE

CLAIM OF PRIORITY

Priority is claimed to International patent application no. PCT/EP2021/064055 filed on May 26, 2021, European patent application no. 20 176 791.0 filed on May 27, 2020, and European patent application no. 20 206 593.4 filed on Nov. 10, 2020.

BACKGROUND

The invention relates to a process for the preparation of a solid allulose material comprising crystalline allulose, the method comprising the steps of (a) providing in an evaporating crystallizer an aqueous mother liquor containing dissolved allulose; (b) maintaining, preferably until the end of crystallization, the aqueous mother liquor within the evaporating crystallizer at a crystallization temperature within the range of from 20 to 80° C.; (c) maintaining, preferably until the end of crystallization, the vapor phase above the aqueous mother liquor within the evaporating crystallizer at a crystallization pressure within the range of from 40 to 500 mbar; and (d) inducing crystallization of allulose from the aqueous mother liquor at the crystallization temperature and at the crystallization pressure in a supersaturated state thereby obtaining the solid allulose material as a precipitate, and a supernatant.

It is known to crystallize allulose from allulose syrups having a high allulose content by adding seed crystals. In conventional processes for obtaining crystalline allulose, crystallization is induced by evaporating solvent (water) and/or cooling the solution. Crystallization is then effected from an oversaturated solution by further increasing the content of dry matter and/or falling below the dissolution temperature.

Various methods for preparing crystalline allulose have been described in the prior art.

CN 104 447 888 discloses preparing a crystal allulose product by virtue of working procedures such as chemical differential phase isomerism, refined chromatography separation and purification, concentration and crystallization and the like by adopting glucose as the raw material.

CN 106 480 125 relates to a method using a solid D-psicose3-epimerase to convert fructose to obtain a conversion solution containing high-concentration D-psicose. A cooling crystallization process is used for crystallizing the conversion solution to obtain the high-concentration D-psicose crystal.

CN 107 699 557 discloses a method for preparation of high-purity D-psicose comprising the step of performing chromatographic separation, concentration, crystallization or drying on a D-psicose solution to obtain D-psicose.

CN 110 627 847 relates to a method for preparing allulose crystals including chromatographic separation of an allulose solution after enzymatic conversion is completed to purify the allulose to a purity of more than 95%. The purified psicose is concentrated to a solid content of 75-85%, and the temperature is quickly reduced to 35-45° C. Seed crystals are added, the temperature is maintained at 35-45° C., and at a vacuum degree of –0.03 to –0.09 MPa, and at constant temperature evaporation crystallization is performed. Centrifugal separation provides crystals with a particle size larger than 60 meshes, which are washed and dried to obtain allulose crystals.

CN 110 872 332 discloses a crystallization process of psicose, which includes the following steps: (1) preliminary crystallization using evaporation crystallization equipment; (2) deep crystallization using cooling crystallization equipment; the process is divided into two steps of crystallization, including preliminary crystallization using evaporative crystallization equipment and deep crystallization using cooling crystallization equipment can obtain psicose crystals with a larger crystal size without using organic solvents.

U.S. Pat. No. 2,011,237 790 relates to a method of producing D-psicose crystals from a D-psicose solution by using supersaturation.

KR 2016 062 349 relates to a method for producing D-psicose having high purity of 99% (w/w) or higher comprising the step of concentrating a D-psicose solution, performing heat exchange cooling on the D-psicose solution, crystallizing the D-psicose solution; performing heat exchange cooling on a crystallization separation base solution, and re-circulating the crystallization separation base solution within a procedure. A continuous chromatography separation fructose base solution and a crystallization separation base solution are collected and fed during an enzyme reaction procedure, so D-psicose may be stably separated through continuous chromatography despite long-term recirculation thereof.

U.S. Pat. No. 2,017,313 734 discloses a method for producing high purity D-psicose crystals having a purity of 98% (w/w) or more and a grain size of MA200 or more. The method includes: removing impurities from a D-psicose solution to obtain a purified D-psicose solution; concentrating the purified D-psicose solution; cooling the concentrated D-psicose solution to 30° C. to 40° C. through a heat exchanger; seed crystallizing the D-psicose solution at 30° C. to 40° C. to obtain a seed crystallized massecuite; and full-scale crystallizing the seed crystallized massecuite. The method can produce pure D-psicose crystals in a suitable form for industrial application through an economical crystallization process from the D-psicose solution without using organic solvents.

WO 2018 087 261 relates to a process for the synthesis of a product saccharide, preferably of D-allulose from an educt saccharide, preferably from D-fructose under heterogeneous or homogeneous catalysis which includes chemical and/or enzymatic catalysis. The synthesis is performed in at least two reactors that are arranged in series and the reaction product exiting the first reactor is subjected to chromatographic separation before it enters the second reactor. Preferably, the chromatographic separation is integrated in a simulated moving bed.

WO 2018 105 931 relates to a method for preparing psicose by introducing and recycling a psicose crystallization mother liquor obtained from a psicose crystallization process into at least one process selected from the group consisting of an activated carbon treatment process, an ion purification process, a simulated moving bed chromatographic separation process, and a process for concentrating a psicose fraction.

U.S. Pat. No. 2,018,327 796 relates to a method of producing D-psicose including the steps of subjecting D-fructose to D-psicose epimerization to produce a D-psicose-containing solution, subjecting the D-psicose-containing solution to first cooling and ion purification, subjecting the purified D-psicose-containing solution to first concentration and second cooling, subjecting the D-psicose-containing solution, which has been subjected to first concentration and second cooling, to chromatography to obtain a D-fructose-containing mother liquor and a D-psicose-containing separated solution, and subjecting the D-psicose-containing separated solution to second concentration and third cooling to obtain D-psicose crystals, wherein the D-fructose-containing mother liquor produced by chromatography is reused in the D-psicose epimerization.

WO 2019 004 554 relates to a method for producing a functional crystalline sweetener, and, more specifically, to a method for producing a crystalline sweetener for improving crystal yield and increasing particle size by controlling the content of impurities included in a solution for producing crystals, or the generation of the impurities.

US 2019 330253 discloses a method for producing D-allulose crystals that allows for a continuous production process and ensures a high yield. A nanofiltration unit is used for producing D-allulose crystals to improve the yield and/or quality of the resulting crystals.

CN 110 872 332 discloses a method for preparing allulose crystals by a two-step process, wherein in a first step an allulose-containing solution is concentrated and preliminary crystallized under reduced pressure and in a second step is deep crystallized via cooling crystallization.

U.S. Pat. No. 2,020,040 023 relates to a method wherein allulose crystals are efficiently produced from an allulose syrup using seed crystals.

U.S. Pat. No. 2,020,062 792 discloses a method for preparing high-purity D-psicose, comprising the step of subjecting a crude D-psicose solution to decolorization, filtration, ion exchange, chromatographic separation, concentration, and then crystallization or drying, obtaining D-psicose.

The known methods for preparing crystalline allulose, however, are not satisfactory in every respect and there is a demand for improved methods. On the one hand, conventional evaporation of solvent under atmospheric pressure requires comparatively high temperatures. This is not only detrimental with respect to energy consumption but additionally leads to degradation reactions and coloration, particularly browning of the crystalline product. On the other hand, conventional cooling crystallization results in a significant increase of solution viscosity towards lower temperatures impeding mixing and distribution of seed crystals. This favors formation of fines and negatively affects crystallization rate.

Further, various conventional processes for crystallization of allulose require altering crystallization conditions over time. Thus, crystallization conditions are not kept essentially constant over time but require careful adjustment of temperature gradients and the like. Such processes are not particularly suited for continuous operation in industrial large scale production.

It is therefore an object of the invention to provide an improved method for the preparation of crystalline allulose. The method should provide allulose crystals in a high yield with good crystalline properties in a simple, timely and cost efficient manner, preferably in a single crystallization step under essentially constant crystallization conditions. Energy consumption should be low and equipment should be conventional.

SUMMARY

This object has been achieved by the subject-matter of the patent claims.

It has been surprisingly found that compared to cooling crystallization where viscosity dramatically increases when temperatures are lowered, higher crystallization rates can be achieved under reduced pressure at constantly moderate temperatures of about 45° C. This results in a space-time-yield that is improved by about 25%.

At temperatures higher than those for cooling crystallization, average viscosity of the aqueous mother liquor is reduced thereby improving material transport (by convection and diffusion). This increases crystallization rate compared to that of cooling crystallization and further facilitates process control, as viscosity remains constant or nearly constant for an extended period of time.

Viscosity may further be maintained at constant levels by continuously supplying fresh aqueous mother liquor such that viscosity only increases at the very end of the overall process when no further fresh aqueous mother liquor is supplied anymore. Continuous supply with fresh aqueous mother liquor further allows for operating under optimized conditions in an oversaturated state without fluctuations which would otherwise have a negative impact of crystal properties. Compared to cooling crystallization, optimized conditions do not need to be achieved by adjusting crystal formation and cooling rate, but in a steady state may simply be maintained by continuous supply with fresh aqueous mother liquor in a controlled fashion. Further, continuous supply of fresh aqueous mother liquor and simultaneous removal of evaporated solvent from the system actually makes available a bigger reactor volume for the crystalline material. This also increases space-time-yield.

Further, it has been surprisingly found that compared to evaporating crystallization at atmospheric pressure or weak vacuum and the correspondingly higher temperatures, degradation reactions can be suppressed under vacuum at constantly moderate temperatures of about 45° C. This results in less mildew and caramel notes upon organoleptic testing.

Still further, it has been surprisingly found that crystallization under reduced pressure at constantly moderate temperatures of about 45° C. provides for improved options of process control and thus allows for preparing larger crystals of equal size, i.e. having a comparatively narrow particle size distribution. The aqueous mother liquor is more homogeneous, because there is no temperature gradient towards cooling surfaces of heat exchangers. This reduces formation of fines thereby allowing for comparatively narrow particle size distributions and finally also for larger crystals. Time factor is compensated by the rate of crystal formation which again is a function of temperature and material transport, i.e. viscosity.

Yet further, it has been surprisingly found that the supersaturation has an impact on the particle size. Supersaturation can be regulated by temperature, pressure and addition of mother liquor. Thus, crystallization conditions can be optimized to avoid fine grain formation with constant supersaturation.

Furthermore, the volume to be added along with seed crystals can be minimized and oversaturation of the aqueous mother liquor can be better controlled thereby yielding larger crystals. Seed crystals may be added in form of suspensions in alcoholic medium. Suitable alcohols include but are not limited to methanol, ethanol, n-propanol, isopropanol, tert-butanol and mixtures thereof. The alcohol is completely or nearly completely evaporated so that at best trace amounts of alcohol are detectable in the final product. The higher vapor pressure of alcohol results in a significantly improved and faster mixing of the aqueous mother liquor (allulose syrup) with the seed crystals at the time of seeding.

Moreover, it has been surprisingly found that static crystallization conditions can be found which on the one hand allow for crystallization under essentially constant conditions and therefore are perfectly suited for industrial large scale crystallization of allulose in a continuous or semi-continuous process (e.g. fed-batch); and which on the other hand provide allulose crystals having an excellent degree of crystallinity and particle size.

It has surprisingly been found that controlled crystallization is also possible under significantly reduced pressure, as a result of which the temperature of the evaporation can be reduced. It has been found that the crystal size is not adversely affected, since the saturation concentration (dry matter) can be kept constant in the metastable range, especially in the fed-batch process, by adding allulose syrup. The faster evaporation is compensated by the addition of allulose syrup in the fed-batch process. A main advantage of the lower pressure is the reduction in temperature, which results in a reduction in by-products. Higher temperatures lead to the formation of undesirable by-products such as hydroxymethylfurfural (HMF).

Compared to evaporative crystallization under normal pressure, significantly less seed crystals have to be used, since the metastable area can be maintained in a much more controlled manner. A variation within the concentration can be adjusted by adding allulose syrup, especially in the fed-batch process. This also minimizes the amount of seed crystal within the solution and greatly reduces the formation of fine grains compared to crystallization under normal pressure.

No heating peaks are required to redissolve fine grain, but continuous pressure and temperature control lead to good results with low process complexity.

A first aspect of the invention relates to a process for the preparation of a solid allulose material comprising crystalline allulose, the method comprising the steps of (a) providing in an evaporating crystallizer an aqueous mother liquor containing dissolved allulose;

(b) maintaining, preferably until the end of crystallization, the aqueous mother liquor within the evaporating crystallizer at a crystallization temperature within the range of from 20 to 80° C.; preferably from 40 to 50° C., more preferably from 40 to 49° C., still more preferably from 40 to 45° C. or from 45 to 50° C., or from 45 to 49° C.;

(c) maintaining, preferably until the end of crystallization, the vapor phase above the aqueous mother liquor within the evaporating crystallizer at a crystallization pressure within the range of from 40 to 500 mbar; preferably from 40 to 200 mbar, more preferably from 40 to 100 mbar, still more preferably 40 to 60 mbar, most preferably 40 to 50 mbar; and (d) inducing crystallization of allulose from the aqueous mother liquor at the crystallization temperature and at the crystallization pressure in a supersaturated state thereby obtaining the solid allulose material as a precipitate, and a supernatant.

The process according to the invention serves the purpose of preparing of a solid allulose material comprising or essentially consisting of crystalline allulose.

The process according to the invention comprises at least steps (a), (b), (c) and (d), which may be performed consecutively, partially or completely simultaneously in any order.

For the purpose of the specification, unless expressly stated otherwise, "allulose" refers to D-allulose. While it is contemplated that D-allulose may also be present in admixture with minor amounts of L-allulose, the content of D-allulose is preferably at least 95 wt.-%, more preferably at least 99 wt.-%, and in particular at least 99.9 wt.-% of the total quantity of D-allulose and L-allulose.

For the purpose of the specification, unless expressly stated otherwise, "until the end of crystallization" refers to the time span from inducing crystallization in step (d) until withdrawal of the solid allulose material, i.e. the precipitate, from the evaporating crystallizer. When the process according to the invention is operated continuously or semi-continuously, the time span is from inducing crystallization in step (d) for the very first time after a previous shut-down of the entire process until a next shut-down of the entire process.

Unless expressly stated otherwise, all percentages are expressed as weight percent (wt.-%).

BRIEF DESCRIPTION OF THE DRAWINGS

FIG. 2 after 1.5 h, FIG. 3 after 21 h, FIG. 4 after 50.5 h, FIG. 5 after 67 h.

Figure 1:
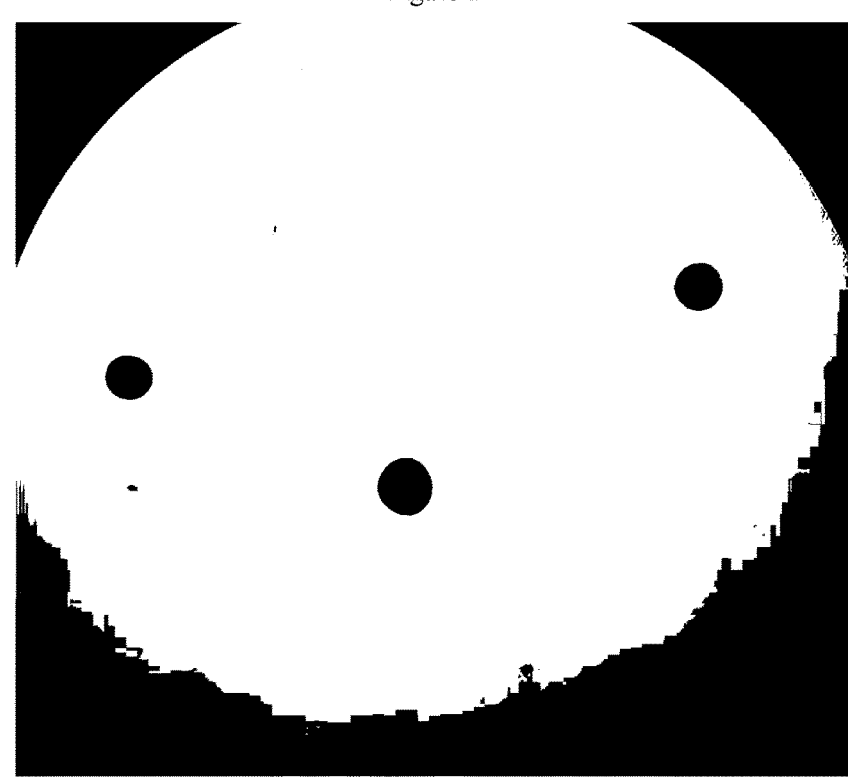
FIG. 1 shows a microscopic image of allulose syrup at inoculation temperature before inoculation.

The process according to the invention is an evaporating crystallization process. Supersaturation is produced by the evaporation of water from the aqueous mother liquor. In the process, the dry substance content of the solution or of the crystal suspension (magma), consisting of allulose crystals and mother liquor, increases. Consequently, either the solubility limit is exceeded and the crystallization process eventually initiated by nucleation or injection of crystallizate (slurry, seed magma crystallizate), or crystals already present are induced to grow.

Preferably, the process according to the invention does not comprise any step of crystallization under atmospheric pressure.

Preferably, the process according to the invention does not comprise any step of cooling crystallization.

In step (a) of the process according to the invention, an aqueous mother liquor containing dissolved allulose is provided in an evaporating crystallizer. While it is contemplated that the aqueous mother liquor may additionally contain undissolved material in suspension, preferably the aqueous mother liquor is a solution, typically an allulose syrup.

Preferably, the aqueous mother liquor (e.g. allulose syrup) originates from a reactor wherein allulose is synthesized from suitable starting materials, preferably from fructose, in an enzymatically catalyzed process. After synthesis of the allulose in the reactor, the product composition that has been withdrawn from the reactor may have undergone work-up, such as desalting, decoloring, purification (e.g. by chromatography), filtration (e.g. nanofiltration), concentrating, or combinations thereof.

Preferably, the aqueous mother liquor (feed syrup) is prepared from thick juice. Optimal thick juice purification should ensure that the thick juice is clear, i.e. that no solids are precipitated in the course of evaporation. However, it is also contemplated that the aqueous mother liquor is prepared from standard liquor or remelt syrup.

Preferably, the aqueous mother liquor (feed syrup) has a constant dry substance content, pH value, color and purity. Purity, dry substance content and temperature should be so mutually attuned that there is no spontaneous supersaturation in the evaporating crystallizer when the feed syrup is drawn in and preferably a flash evaporation takes place.

Preferably, the aqueous mother liquor (feed syrup) is homogenized. This can be achieved by mixing run-off syrups in a tank equipped with a stirrer, adjusting to the desired dry substance content by adding water (preferably condensate) and warming by pumping through a heater. In a preferred embodiment, the feed syrup is sterilized this way.

Preferably, the aqueous mother liquor provided in step (a) has a content of dry matter of at least 80 wt.-%; preferably at least 82 wt.-%; more preferably at least 84 wt.-%; relative to the total weight of the aqueous mother liquor.

Preferably, the aqueous mother liquor provided in step (a) has a density within the range of from 1.36 to 1.46 g cm$^{-3}$; preferably from 1.38 to 1.44 g cm$^{-3}$.

Preferably, the aqueous mother liquor provided in step (a) has an allulose content of at least 90 wt.-%; preferably at least 95 wt.-%; more preferably at least 98 wt.-%; still more preferably at least 99 wt.-%; in each case relative to the total content of dry matter that is contained in the aqueous mother liquor.

Preferably, the aqueous mother liquor provided in step (a) has a fructose content of at most 10 wt.-%; preferably at most 5.0 wt.-%; more preferably at most 2.5 wt.-%; in each case relative to the total content of dry matter that is contained in the aqueous mother liquor.

Preferably, the aqueous mother liquor provided in step (a) has a fructose content of at least 0.1 wt.-%; preferably at least 0.5 wt.-%; more preferably at least 1.0 wt.-%; relative to the total content of dry matter that is contained in the aqueous mother liquor.

Preferably, the aqueous mother liquor provided in step (a) has a fructose content of at most 10 wt.-%; preferably at most 5.0 wt.-%; more preferably at most 2.5 wt.-%; relative to the total weight of the aqueous mother liquor.

Preferably, the aqueous mother liquor provided in step (a) has a fructose content of at least 0.1 wt.-%; preferably at least 0.5 wt.-%; more preferably at least 1.0 wt.-%; relative to the total weight of the aqueous mother liquor.

Preferably, the aqueous mother liquor provided in step (a) has a content of components other than allulose (i.e. total impurities) of at most 10 wt.-%; preferably at most 5.0 wt.-%; more preferably at most 2.5 wt.-%; in each case relative to the total content of dry matter that is contained in the aqueous mother liquor. In general, these impurities can, on the one hand, modify the solution characteristics, and, on the other hand, interact with the growing crystal surface. The interaction of these impurities with the allulose in the aqueous mother liquor can both modify the physical characteristics of the solution and vary the allulose solubility; anyway crystallization kinetics will be influenced. The actual supersaturation being equal, the crystal growth rate typically decreases with the increase of impurity concentration, although the influence exerted can depend upon the nature and relative individual concentration of impurities. The presence of impurities decreases the overall mass transfer and crystallization rates.

Preferably, the aqueous mother liquor provided in step (a) has a content of allulose of at least 80 wt.-%; preferably at least 82 wt.-%; more preferably at least 84 wt.-%; relative to the total weight of the aqueous mother liquor.

Preferably, the aqueous mother liquor provided in step (a) essentially consists of allulose, residual by-products obtained in the course of allulose synthesis and not removed by purification, residual starting materials not converted in the course of allulose synthesis and not removed by purification, and water. Preferably, the aqueous mother liquor provided in step (a) essentially contains no liquids (solvents) other than water. However, it is contemplated that minor amounts of alcohol may be present, which are preferably entrained by seeding with crystals that are provided as suspensions (slurries) in alcohol or in alcoholic medium.

In a preferred embodiment, the process according to the invention involves evaporating crystallization under isothermal conditions.

In step (b) of the process according to the invention, the aqueous mother liquor within the evaporating crystallizer is maintained at a crystallization temperature within the range of from 20 to 80° C.; preferably from 40 to 50° C., more preferably from 40 to 49° C., still more preferably from 40 to 45° C. or from 45 to 50° C., or from 45 to 49° C.

Depending upon previous processing of material, the aqueous mother liquor may require heating or cooling until the predetermined crystallization temperature is reached. Preferably, the crystallization temperature is adjusted and maintained by conventional equipment. Suitable heating devices and cooling devices are known to the skilled person. Preferably, crystallization temperature is continuously monitored and regulated. In a preferred embodiment, the dry substance content of the aqueous mother liquor is measured and the crystallization temperature is regulated according to the measured value for the dry substance content.

Preferably, the crystallization temperature is within the range of from 29 to 80° C.; preferably 36 to 80° C.; more preferably 41 to 80° C.; still more preferably 42 to 80° C., yet more preferably 43 to 80° C.; most preferably 45±3° C.; and in particular 45±2° C. In preferred embodiments, the crystallization temperature is within the range of 43.4±3.5° C., preferably 43.4±3.0° C., more preferably 43.4±2.5° C., still more preferably 43.4±2.0° C., yet more preferably 43.4±1.5° C., even more preferably 43.4±1.0° C., most preferably 43.4±0.5° C.

Preferably, the crystallization temperature is at least 29° C., or at least 31° C., or at least 33° C., or at least 35° C., or at least 37° C., or at least 39° C., or at least 41° C., or at least 43° C., or at least 45° C., or at least 47° C., or at least 49° C., or at least 51° C., or at least 53° C., or at least 55° C.

Preferably, the crystallization temperature is at most 79° C., or at most 77° C., or at most 75° C., or at most 73° C., or at most 71° C., or at most 69° C., or at most 67° C., or at most 65° C., or at most 63° C., or at most 61° C., or at most 59° C., or at most 57° C., or at most 55° C.

Preferably, the crystallization temperature is kept essentially constant over time, preferably until the end of crystallization; preferably the crystallization temperature does not change relatively by more than 2.0° C.; preferably by not more than 1.5° C.; more preferably by not more than 1.0° C.; most preferably by not more than 0.5° C.

In other preferred embodiments, the crystallization temperature is increased in the course of crystallization as the dry substance content increases. Preferably, crystallization is commenced at a crystallization temperature $T_0$ and terminated at a crystallization temperature $T_1$, wherein preferably $T_1 \geq T_0$, more preferably $T_1 > T_0$. Preferably, the crystallization temperature is steadily increased. Preferably, during the entire process the given crystallization temperature T is greater than or equal $T_0$.

In preferred embodiments, the relative increase of the crystallization temperature $T_1 - T_0$ is at least 0.5° C., more preferably at least 1.0° C., still more preferably at least 1.5°

C., yet more preferably at least 2.0° C., even more preferably at least 2.5° C., most preferably at least 3.0° C., and in particular at least 3.5° C.

In preferred embodiments, the relative increase of the crystallization temperature $T_1-T_0$ is at most 10° C., more preferably at most 9.5° C., still more preferably at most 8.0° C., yet more preferably at most 7.5° C., even more preferably at most 7.0° C., most preferably at most 6.5° C., and in particular at most 6.0° C.

Preferably, step (b) of the process according to the invention additionally includes maintaining, preferably until the end of crystallization, the vapor phase above the aqueous mother liquor at a vapor temperature within the range of from 25 to 65° C.; preferably 29 to 60° C. Preferably, the vapor temperature is adjusted and maintained by conventional equipment. Suitable heating devices and cooling devices are known to the skilled person. Preferably, vapor temperature is continuously monitored and regulated.

Preferably, the vapor temperature is at least 25° C., or at least 27° C., or at least 29° C., or at least 31° C., or at least 33° C., or at least 35° C., or at least 37° C., or at least 39° C., or at least 41° C., or at least 43° C., or at least 45° C., or at least 47° C., or at least 49° C., or at least 51° C., or at least 53° C., or at least 55° C.

Preferably, the vapor temperature is at most 65° C., or at most 63° C., or at most 61° C., or at most 59° C., or at most 57° C., or at most 55° C.

Preferably, the vapor phase above the aqueous mother liquor is kept over time at an essentially constant vapor temperature; preferably the vapor temperature does not change relatively by more than 2.0° C.; preferably by not more than 1.5° C.; more preferably by not more than 1.0° C.; most preferably by not more than 0.5° C.

In another preferred embodiment, the process according to the invention involves evaporating crystallization under isobaric conditions.

In step (c) of the process according to the invention, the vapor phase above the aqueous mother liquor within the evaporating crystallizer is maintained at a crystallization pressure within the range of from 40 to 500 mbar; preferably from 40 to 200 mbar.

Depending upon previous processing of material, the vapor phase above the aqueous mother liquor within the evaporating crystallizer may require evacuation until the predetermined crystallization pressure is reached. Preferably, the crystallization pressure is adjusted and maintained by conventional equipment. Suitable evacuation devices and vents are known to the skilled person. Preferably, crystallization pressure is continuously monitored and regulated.

Preferably, the crystallization pressure is at least 40 mbar, or at least 41 mbar, or at least 42 mbar, or at least 43 mbar, or at least 44 mbar, or at least 45 mbar, or at least 46 mbar. Preferably, the crystallization pressure is at least 60 mbar, or at least 61 mbar, or at least 62 mbar, or at least 63 mbar, or at least 64 mbar, or at least 65 mbar, or at least 66 mbar.

Preferably, the crystallization pressure is at most 200 mbar, or at most 180 mbar, or at most 160 mbar, or at most 140 mbar, or at most 120 mbar, or at most 100 mbar, or at most 90 mbar, or at most 80 mbar, or at most 70 mbar, or at most 65 mbar, or at most 64 mbar, or at most 63 mbar, or at most 62 mbar, or at most 61 mbar, or at most 60 mbar.

Preferably, the crystallization pressure is within the range of from 40 to 200 mbar; or 45 to 200 mbar; or 46 to 200 mbar; more preferably 40 to 100 mbar; or 45 to 100 mbar; or 46 to 100 mbar; most preferably 40 to 60 mbar; or 45 to 60 mbar; or 46 to 60 mbar. Preferably, the crystallization pressure is within the range of from 60 to 200 mbar; more preferably 61 to 200 mbar; still more preferably 62 to 200 mbar; yet more preferably 60 to 100 mbar; even more preferably 61 to 100 mbar; and most preferably 62 to 100 mbar.

Preferably, the crystallization pressure is kept essentially constant over time, preferably until the end of crystallization; preferably the crystallization pressure does not change relatively by more than 20 mbar; preferably by not more than 15 mbar; more preferably by not more than 10 mbar; most preferably by not more than 5 mbar.

In preferred embodiments of the process according to the invention, crystallization temperature, vapor temperature and crystallization pressure independently of one another are kept essentially constant over time in the course of crystallization, i.e. from the very beginning of crystallization until the very end of crystallization (i.e. which is not followed by any subsequent additional crystallization under same or different conditions).

Preferably, crystallization temperature, vapor temperature and crystallization pressure independently of one another do not deviate by more than 10%, more preferably by not more than 8%, more preferably by not more than 6%, still more preferably by not more than 4%, from the initial value that was set at the very beginning of crystallization. For example, when the crystallization temperature is initially set at X° C., the vapor temperature is initially set at Y° C. and the crystallization pressure is initially set at Z mbar, in the course of the entire crystallization until its end, the crystallization temperature, the vapor temperature and the crystallization pressure independently of one another are within the range of X° C.±10%, Y° C.±10%, and Z mbar±10%, respectively.

In another preferred embodiment, the process according to the invention involves evaporating crystallization under conditions between isothermal conditions and isobaric conditions.

In particularly preferred embodiments, the crystallization pressure is within the range of from 40 to 50 mbar and the crystallization temperature is within the range of from 40 to 50° C., preferably from 41 to 50° C., more preferably from 42 to 50° C., still more preferably from 43 to 50° C.

In step (d) of the process according to the invention, crystallization of allulose from the aqueous mother liquor is induced at the crystallization temperature and at the crystallization pressure in a supersaturated state thereby obtaining the solid allulose material as a precipitate and a supernatant.

Crystallization of allulose from the aqueous mother liquor is induced in a supersaturated state, i.e. when the supersaturation coefficient y is greater than 1. The supersaturation coefficient y results from the division of the ratio of the mass fraction of allulose to water in a solution by the ratio of the mass fraction of allulose to water in a saturated solution at a given temperature. It shows whether an aqueous mother liquor is unsaturated (y<1), saturated (y=1) or supersaturated (y>1). At a given temperature, the supersaturated state can be divided into a metastable zone (1<y≤1.2), an intermediate zone (1.2<y<1.3), and a labile zone (1.3≤y).

In a preferred embodiment, crystallization of allulose from the aqueous mother liquor is induced at the crystallization temperature and at the crystallization pressure in said metastable zone of the supersaturated state (1<y≤1.2). Within the metastable zone, the growth of a seed crystal proceeds, together with a slight nucleation probability.

The metastable zone is particularly preferred, while in certain instances crystallization may even be promoted at supersaturation coefficients y slightly below 1.00, e.g. 0.98.

Ensuring good circulation in the evaporating crystallizer and keeping supersaturation in the metastable zone (supersaturation coefficient y<1.2), particularly when the crystal size is comparatively small, suppresses formation of undesirable twins and conglomerates.

Preferably, in step (d) of the process according to the invention crystallization is induced at a supersaturation coefficient y of the aqueous mother liquor of at least 0.95, or at least 0.96, or at least 0.97, or at least 0.98, or at least 0.99, or at least 1.00, or at least 1.01, or at least 1.02, or at least 1.03, or at least 1.04, or at least 1.05, or at least 1.06, or at least 1.07, or at least 1.08, or at least 1.09, or at least 1.10, or at least 1.11, or at least 1.12, or at least 1.13, or at least 1.14, or at least 1.15, or at least 1.16, or at least 1.17, or at least 1.18, or at least 1.19, or at least 1.20.

Preferably, in step (d) of the process according to the invention crystallization is induced at a supersaturation coefficient y of the aqueous mother liquor of at least 1.00.

Preferably, in step (d) of the process according to the invention crystallization is induced at a supersaturation coefficient y of the aqueous mother liquor of at least 1.01.

Preferably, in step (d) of the process according to the invention crystallization is induced at a supersaturation coefficient y of the aqueous mother liquor of at least 1.02.

Preferably, in step (d) of the process according to the invention crystallization is induced at a supersaturation coefficient y of the aqueous mother liquor of at least 1.03.

Preferably, in step (d) of the process according to the invention crystallization is induced at a supersaturation coefficient y of the aqueous mother liquor of at least 1.04.

Preferably, in step (d) of the process according to the invention crystallization is induced at a supersaturation coefficient y of the aqueous mother liquor of at least 1.05.

Preferably, in step (d) of the process according to the invention crystallization is induced at a supersaturation coefficient y of the aqueous mother liquor of at most 1.20, or at most 1.19, or at most 1.18, or at most 1.17, or at most 1.16, or at most 1.15, or at most 1.14, or at most 1.13, or at most 1.12, or at most 1.11, or at most 1.10, or at most 1.09, or at most 1.08, or at most 1.07, or at most 1.06, or at most 1.05, or at most 1.04, or at most 1.03, or at most 1.02, or at most 1.01, or at most 1.00, or at most 0.99, or at most 0.98, or at most 0.97, or at most 0.96.

Preferably, in step (d) of the process according to the invention crystallization is induced at a supersaturation coefficient y of the aqueous mother liquor of at most 1.06.

Preferably, in step (d) of the process according to the invention crystallization is induced at a supersaturation coefficient y of the aqueous mother liquor of at most 1.05.

Preferably, in step (d) of the process according to the invention crystallization is induced at a supersaturation coefficient y of the aqueous mother liquor of at most 1.04.

Preferably, in step (d) of the process according to the invention crystallization is induced at a supersaturation coefficient y of the aqueous mother liquor of at most 1.03.

Preferably, in step (d) of the process according to the invention crystallization is induced at a supersaturation coefficient y of the aqueous mother liquor of at most 1.02.

Preferably, in step (d) of the process according to the invention crystallization is induced at a supersaturation coefficient y of the aqueous mother liquor of at most 1.01.

Preferably, in step (d) of the process according to the invention crystallization is induced at a supersaturation coefficient y of the aqueous mother liquor within the range of 0.97±0.05, or 0.99±0.10, or 0.99±0.05, or 1.01±0.10, or 1.01±0.05, or 1.03±0.10, or 1.03±0.05, or 1.05±0.10, or 1.05±0.05, or 1.07±0.10, or 1.07±0.05, or 1.09±0.10, or 1.09±0.05, or 1.11±0.10, or 1.11±0.05, or 1.13±0.10, or 1.13±0.05, or 1.15±0.10, or 1.15±0.05.

In another preferred embodiment, crystallization of allulose from the aqueous mother liquor is induced at the crystallization temperature and at the crystallization pressure in said intermediate zone of the supersaturated state (1.2<y<1.3), wherein the probability of nucleation becomes higher.

In a further preferred embodiment, crystallization of allulose from the aqueous mother liquor is induced at the crystallization temperature and at the crystallization pressure in said labile zone of a supersaturated state (1.3≤y), wherein the probability of nucleation becomes very high.

Starting from an undersaturated solution a supersaturated solution can be obtained by (i) increasing the allulose concentration, (ii) by decreasing the temperature, or (iii) through flash evaporation. According to the invention, the supersaturated state is typically achieved by increasing the allulose concentration as a consequence of evaporation under reduced pressure.

When the process according to the invention is operated in the batch mode, at the end of the process, precipitate and supernatant may be withdrawn from the evaporating crystallizer and may be separated from one another, e.g. by filtration and/or centrifugation. When the process according to the invention is operated continuously or semi-continuously, however, the supernatant or at least a portion thereof remains within the evaporating crystallizer and is admixed with fresh aqueous mother liquor that is additionally supplied to the evaporating crystallizer.

Preferably, the supernatant obtained in step (d) of the process according to the invention has a content of dry matter of at most 78 wt.-%; preferably at most 76 wt.-%; more preferably within the range of from 70 to 75 wt.-%; relative to the total weight of the supernatant.

Preferably, the at least a portion of the supernatant obtained in step (d) is recycled to step (a) of the process according to the invention.

Preferably, step (d) of the process according to the invention comprises the substeps of (d-1) (i) evaporating water from the aqueous mother liquor thereby increasing the concentration of dissolved allulose until spontaneous crystallization occurs and/or (ii) inducing crystallization by means of seed crystals;

(d-2) promoting crystal growth by adding further aqueous mother liquor; and (d-3) withdrawing precipitate from the evaporating crystallizer.

Preferably, the crystallization temperature at all substeps is kept essentially constant overtime, preferably until the end of crystallization; preferably the crystallization temperature at all substeps does not change relatively by more than 2.0° C.; preferably by not more than 1.5° C.; more preferably by not more than 1.0° C.; most preferably by not more than 0.5° C.

Preferably, the crystallization pressure at all substeps is kept essentially constant over time, preferably until the end of crystallization; preferably the crystallization pressure at all substeps does not change relatively by more than 20 mbar; preferably by not more than 15 mbar; more preferably by not more than 10 mbar; most preferably by not more than 5 mbar.

Preferably, in step (d) of the process according to the invention, crystallization is induced by means of seed crystals.

Preferably, the number of crystals of crystalline allulose obtained by the process according to the invention is at most 150% of the number of seed crystals that are employed, more preferably at most 140%, still more preferably at most 130%, yet more preferably at most 120%, even more preferably at most 110%, most preferably at most 105%, and in particular at most 101% of the number of seed crystals that are employed. Preferably, the number of crystals of crystalline allulose obtained by the process according to the invention essentially corresponds to the number of seed crystals that are employed.

In a preferred embodiment, the seed crystals are added to the aqueous mother liquor that is contained in the evaporating crystallizer.

In another preferred embodiment, the seed crystals are added to the aqueous mother liquor before it is supplied to the evaporating crystallizer.

The seed crystals are preferably provided in form of slurry or magma.

Preferably, the seed crystals are provided in form of a suspension in an alcoholic liquid, which is added to the aqueous mother liquor.

Preferably, the alcoholic liquid comprises methanol, ethanol, n-propanol, iso-propanol, tertbutanol or any combination thereof.

Preferably, the volume of the suspension is at most 1.0 vol.-% of the volume of the aqueous mother liquor that is contained in the evaporating crystallizer.

In a preferred embodiment, step (d) of the process according to the invention comprises adding a suspension of seed crystals in an alcoholic liquid, preferably seed slurry, to the aqueous mother liquor;

maintaining, preferably until the end of crystallization, the vapor phase above the aqueous mother liquor within the evaporating crystallizer for a first time period at a first crystallization pressure within the range of from 50 to 200 mbar;

reducing the crystallization pressure from the first crystallization pressure to a second crystallization pressure within the range of from 40 to 100 mbar; and maintaining, preferably until the end of crystallization, the second crystallization pressure for a second time period until the end of crystallization; wherein the second crystallization pressure is kept essentially constant during the second time period; preferably the second crystallization pressure does not change relatively by more than 20 mbar; preferably by not more than 15 mbar; more preferably by not more than 10 mbar; most preferably by not more than 5 mbar.

Preferably, the first crystallization pressure is within the range of 80±20 mbar and the second crystallization pressure is within the range of 50±10 mbar. Preferably, the first time period is shorter than the second time period.

The suspension of seed crystals in an alcoholic liquid (seed slurry) is preferably prepared by wet-milling an allulose/alcohol suspension in a mill, e.g. a ball mill. Following standard routine ensures a consistent product in respect of solids content, number of crystals per unit of volume, and mean crystal size. The ratio of alcohol to allulose is preferably within the range of from 3:1 to 1:1, more preferably 2.5:1 to 2:1. Grinding may take several hours. Preferably, stirrer power is at least 10 kW/m$^3$ to achieve a low percentage of conglomerates by break up. In a preferred embodiment, the slurry is aged for 2 to 6 weeks before use. Preferably, the seed slurry contains 30 to 40 wt.-% crystals, which preferably have a mean crystal diameter d' within the range of from 5 to 15 μm, preferably of about 10 μm. Preferably, the crystal size distribution is relatively uniform (coefficient preferably ≤4, more preferably ≤2.5, still more preferably about 2.0). Preferably, the proportion of conglomerates is less than 10% of the total number of crystals present.

It is also contemplated to prepare the seed slurry by milling allulose in suspension in vegetable oil instead of alcohol.

In another preferred embodiment, step (d) of the process according to the invention comprises adding a suspension of seed crystals in an aqueous non-alcoholic liquid, preferably seed magma, to the aqueous mother liquor; and maintaining, preferably until the end of crystallization, the vapor phase above the aqueous mother liquor within the evaporating crystallizer at the crystallization pressure until the end of crystallization; wherein the crystallization pressure is kept essentially constant over time, preferably until the end of crystallization; preferably the crystallization pressure does not change relatively by more than 20 mbar; preferably by not more than 15 mbar; more preferably by not more than 10 mbar; most preferably by not more than 5 mbar.

In technical evaporating crystallizers, accuracy of supersaturation management is limited, even with mechanical circulation and appropriate measuring devices, because of temperature inhomogeneities. This is particularly the case when a high dry substance content in the feed syrup is sought. Seed magma work circumvents these difficulties. The procedure aims at producing a model crystallizate (seed) which, in the form of seed magma, is injected into a crystallizer containing a syrup having the necessary supersaturation, and which provides enough crystal surface area for the following crystallization process to suppress undesirable secondary nucleation even in pure, highly concentrated feed solutions (aqueous mother liquors). The model crystallizate forms the basis or core of the product crystallizate and influences, in accordance with its quality parameters, in proportion to its mass, the quality of the end product.

The suspension of seed crystals in an aqueous non-alcoholic liquid (seed magma) is preferably essentially free of air bubbles and fines. It is preferably prepared from an allulose mingling syrup.

The mingling syrup is prepared, then preferably raised to a higher temperature, before it is mixed with the colder allulose, in order to attain the desired magma temperature, which preferably corresponds to the crystallization temperature.

The mingler is preferably designed that not only fines are essentially completely dissolved, thus significantly reducing the number of particles, but also to allow air bubbles to escape from the magma. Mingling is preferably carried out in two stages. Part only, e.g. 30% of the total volume of run-off (syrup) required, is added to the mass of allulose in a first stage, which is followed by thorough mixing. Then, in a second stage, the remainder of the run-off (syrup) is added and the resulting total volume is simultaneously homogenized by stirring. The first stage mixing is preferably carried out in a horizontal screw conveyor into which the allulose and the first fraction of run-off (syrup) are fed. From the outlet of the screw conveyor the mixture is transferred to the inlet of a blending chamber. The second fraction of the run-off (syrup) is preferably injected into the mixture at the inlet to the blending chamber. From the first-stage screw conveyor, the mixture is preferably transferred to the blending chamber via a stirring device which breaks up any agglomerations of crystals. The two-stage addition of run-off syrup avoids incorporation of air.

The possibility of controlling the crystal parameters (mean crystal size, crystal size distribution) by means of seed magma work is particularly important in the context of continuous evaporating crystallization. In continuous operation, in contrast to batch work, there is typically a broadening of the crystal size distributions, which depends on the number of compartments of the continuous evaporating crystallizer, as well as the amount of seed magma used and its crystal parameters (mean size and size distribution). The preparation of a seed magma crystallizate having a sufficiently narrow crystal size distribution is therefore one of the process prerequisites for working with continuous evaporating crystallizers, regardless of the purity level at which they are employed.

Preferably, the aqueous mother liquor at the crystallization temperature has a viscosity of at most 2000 mPa·s, or at most 1950 mPa·s, or at most 1900 mPa·s, or at most 1850 mPa·s, or at most 1800 mPa·s, or at most 1750 mPa·s, or at most 1700 mPa·s, or at most 1650 mPa·s, or at most 1600 mPa·s, or at most 1550 mPa·s, or at most 1500 mPa·s, in each case measured by means of a rotary viscosimeter at a speed of 100 rpm.

Preferably, the viscosity of the aqueous mother liquor within the evaporating crystallizer is kept essentially constant over time, preferably until the end of crystallization; preferably the viscosity does not change relatively by more than 100 mPa·s; more preferably by not more than 80 mPa·s; still more preferably by not more than 60 mPa·s; most preferably by not more than 40 mPa·s; and in particular by not more than 20 mPa·s.

In a preferred embodiment, the process according to the invention is operated as a batch process. For this mode of operation, a batch evaporating crystallizer is preferably used.

Compared with continuous evaporating crystallization, advantages of batch evaporating crystallization include:
allulose with a narrow range of particle size distribution (low coefficient of variation) can be produced more easily;
syrups having purities above 98% can be processed more easily;
seed magma can be produced in an integrated operation inside the crystallizers;
incrustations do not require periodic boil-outs; and
no adaptation of the heating surface area to the rate of evaporation required for the crystallization.

Preferably, the batch operation of the process according to the invention may involve any one, a subset or all of the following successive stages; a skilled person recognizes that modifications are possible, which are also contemplated:
(i) Feed phase—the aqueous mother liquor (syrup) to be crystallized (feed syrup, fresh aqueous mother liquor) is drawn into the evaporating crystallizer in which preferably the interior pressure has already been lowered. Preferably, the evaporating crystallizer is equipped with a stirrer that is preferably started as soon as it is submerged deeply enough in the aqueous mother liquor.
(ii) Concentration phase—water evaporation is considerably raised by increasing the flow of heating steam. The agitating effect of the vapor bubbles (bubble boiling) promotes turbulence and with it heat transfer on the juice side. During the concentration phase, depending on the evaporation, more feed syrup may be drawn in in order to maintain a constant level in the crystallizer.
(iii) Seeding point—when crystallization is to be induced by means of seed crystals, the concentration phase ends as soon as the supersaturation required for crystallization is reached (seeding point). Supersaturation at the seeding point depends on the purity of the aqueous mother liquor. When slurry is used for seeding, the supersaturation coefficient preferably ranges from 1.1 to 1.2. When seed magma is used for seeding, the supersaturation coefficient preferably ranges from 0.95 to 1.05 at the seeding point, i.e. the injection of seed magma.
(iv) Crystal formation phase—particularly when seed slurry is used for seeding, after the seeding point the desired growth of the imported crystals is achieved over a certain time, sometimes about e.g. 10 minutes. Preferably, the syrup feed is interrupted in this phase. In order to maintain the supersaturation coefficient as constant as possible, evaporation is preferably reduced by throttling down the steam supply or offset by drawing in water so that crystals<10 μm are dissolved. At the end of the crystal formation phase, the crystal content preferably reaches about 10% and the individual crystals are typically easily visible to the naked eye (typical crystal size about 50 μm). However, when seed magma crystallizate is used for seeding, the crystal formation phase is preferably omitted; then there is just a delay until enough seed magma is drawn in and uniformly distributed.
(v) Crystal growth phase—water evaporation is again increased e.g. by opening the steam supply, and at the same time the supersaturation of the aqueous mother liquor is held as constant as possible in the metastable zone by drawing in more syrup to compensate for evaporation. Whereas the level in the crystallizer remained essentially constant in the feed phase, it steadily rises in the crystal growth phase until at the end the crystal suspension preferably occupies the entire usable volume of the evaporating crystallizer. Associated with the increased level in the evaporating crystallizer is a rise in the boiling temperature on the heating surface. Consequently, even at constant vapor space pressure, the temperature of the crystal suspension preferably increases during this phase within the range according to the invention.
(vi) Tightening phase—during this phase, once the maximum level in the evaporating crystallizer has been reached, no further syrup is drawn in and concentration continues until the desired crystal content is reached, typically about e.g. 55%. This point may be determined e.g. by measuring either the dry substance content of the crystal suspension or its consistency, which can be done indirectly, e.g. by gauging the power uptake of the stirrer motor. In a preferred embodiment, the evaporating crystallizer is combined with a strike receiver in one unit, i.e. placed upon each other and connected by a pipe. This allows for a further increase of crystal content. The magma is then diluted in the mixer with a syrup of calibrated dry substance content and temperature. At the conclusion of the tightening phase, the stirrer is preferably shut off, as is the steak feed and the connection to the condenser. The evaporating crystallizer can be emptied if there is sufficient room in the strike receiver located below for the crystal suspension produced. For this purpose, the vapor space of the evaporating crystallizer is preferably first restored to normal pressure.
(vii) Discharge phase—emptying of the evaporating crystallizer preferably begins with opening of the discharge valve. The empty crystallizer is then preferably cleaned with steam to remove residual crystal suspension adhering to the walls and calandria. Once cleaned, the evaporating crystallizer is ready for the next cycle, after the interior pressure has been restored gradually.

In another preferred embodiment, the process according to the invention is operated as a continuous or semi-continuous process. For this mode of operation, a continuous evaporating crystallizer is preferably used.

In a particularly preferred embodiment, the process according to the invention is operated as a fed-batch process. A typical fed-batch process according to the invention comprises the following stages:

(i) preparation stage: at least partially filling the evaporating crystallizer with the aqueous mother liquor (syrup) to be crystallized (feed syrup, fresh aqueous mother liquor);

(ii) first batch stage: performing evaporating crystallization;

(iii) feed stage: supplying fresh aqueous mother liquor to the evaporating crystallizer;

(iv) second batch stage: performing evaporating crystallization; and (v) optionally, end stage: emptying of the evaporating crystallizer.

In the feed stage (i.e. stage (iii)), fresh aqueous mother liquor is preferably supplied to the evaporating crystallizer when or after a certain predetermined condition has been achieved in the course of the first batch stage (i.e. stage (ii)). Preferably, said predetermined condition is selected from the group consisting of a. viscosity of the aqueous mother liquor within the evaporating crystallizer;

b. density of the aqueous mother liquor within the evaporating crystallizer;

c. dry substance mass of the aqueous mother liquor within the evaporating crystallizer;

d. particle size of the precipitate that is withdrawn from the evaporating crystallizer;

e. torque at a stirred stirring the aqueous mother liquor within the evaporating crystallizer;

f. volume of the aqueous mother liquor within the evaporating crystallizer;

g. yield of the precipitate that has been withdrawn from the evaporating crystallizer;

h. volume or weight of water that has been evaporated and withdrawn from the evaporating crystallizer;

i. evaporation rate;

j. supersaturation coefficient y of the aqueous mother liquor within the evaporating crystallizer;

k. crystallization pressure; and l. crystallization temperature.

In preferred embodiments, in the feed stage (i.e. stage (iii)) the stream of fresh starting material is regulated.

In preferred embodiments, the stream of fresh starting material is regulated when a predetermined condition has been achieved. For this purpose, a characteristic parameter that is indicative for said condition is preferably measured and the supply of fresh aqueous mother liquor to the evaporating crystallizer is commenced when a predetermined value has been achieved. Preferably, the supply of fresh aqueous mother liquor to the evaporating crystallizer is regulated according to the measured value.

For example, the predetermined condition may be the volume of the aqueous mother liquor in the evaporating crystallizer. The initial volume $V_i$ of the aqueous mother liquor in the evaporating crystallizer at the preparation stage (i.e. stage (i)) will typically be reduced in the course of performing evaporating crystallization at the first batch stage (i.e. stage (ii)) due to evaporation and/or withdrawal of crystallizate. In consequence, the volume $V_{ii}$ of the aqueous mother liquor in the evaporating crystallizer at the end of evaporating crystallization at the first batch stage (i.e. stage (ii)) will be smaller than the initial volume $V_i(V_{ii}<V_i)$. In preferred embodiments, a particular value for volume $V_{ii}$ may be predetermined and once said value has been reached, stage (ii) ends and stage (iii) commences, i.e. fresh aqueous mother liquor is supplied to the evaporating crystallizer.

In preferred embodiments, the stream of fresh starting material is regulated in order to keep said predetermined condition essentially constant. For this purpose, a characteristic parameter that is indicative for said condition is preferably measured and the supply of fresh aqueous mother liquor to the evaporating crystallizer is regulated according to the measured value to keep said predetermined condition of the aqueous mother liquor within the evaporating crystallizer essentially constant. Thus, in the above example, the volume of the aqueous mother liquor in the evaporating crystallizer, or alternatively another characteristic parameter that is indicative for the volume, is measured and the supply of fresh aqueous mother liquor to the evaporating crystallizer is regulated according to the measured value to keep the volume of the aqueous mother liquor within the evaporating crystallizer essentially constant; any forthcoming decrease of the volume due to evaporation and/or withdrawal of crystallizate in the course of the second batch stage (i.e. stage (iv)) is then substituted by fresh aqueous mother liquor that is supplied to the evaporating crystallizer.

In other, more preferred embodiments, the stream of fresh starting material is regulated in order to alter said predetermined condition until another predetermined condition has been achieved. For this purpose, a characteristic parameter that is indicative for said condition is preferably measured and the supply of fresh aqueous mother liquor to the evaporating crystallizer is regulated according to the measured value to alter said predetermined condition of the aqueous mother liquor within the evaporating crystallizer until said another predetermined condition has been achieved. Thus, in the above example, the volume of the aqueous mother liquor in the evaporating crystallizer, or alternatively another characteristic parameter that is indicative for the volume, is measured and the supply of fresh aqueous mother liquor to the evaporating crystallizer is regulated according to the measured value to alter (increase) the volume of the aqueous mother liquor within the evaporating crystallizer until another predetermined volume $V_{iii}$ has been achieved ($V_{iii}>V_{ii}$). The second batch stage (i.e. stage (iv)) may then start at increased volume $V_{iii}$. In preferred embodiments, said another predetermined condition essentially corresponds to the initial condition at the preparation stage (i.e. stage (i); in the example, $V_i=V_{iii}$).

In this particularly preferred embodiment, stages (iii) and (iv) can be carried out in chronological order, e.g. one after the other;

simultaneously; or or partially simultaneously.

In this particularly preferred embodiment, stages (iii) and (iv) are carried out repeatedly until the end of crystallization. Preferably, stages (iii) and (iv) are carried out at least 2 times in a week, preferably at least 3 times in a week, more preferably at least 4 times in a week, still more preferably at least 5 times in a week, yet more preferably at least 6 times in a week, most preferably at least 7 times in a week.

Preferred continuous evaporating crystallizers include but are not limited to multi-chamber cascade evaporating crystallizers with magma transport, e.g. continuous evaporating crystallization towers (VKT, Verdampfungs-Kristallisations-Turm), or horizontal multichamber cascade evaporating crystallizers (VKH, Verdampfungs-Kristallisator Horizontal);

multi-chamber crystallizers without transport of magma, e.g. FCB evaporating crystallizers (FCB=Five Fives Cail Babcock), Tongaat-Hulett system evaporating crystallizers, or SRI continuous crystallizers (SRI=Sugar Research Institute); or Langreney continuous crystallizers.

Preferred continuous evaporating crystallizers include but are not limited to mixed suspension mixed product removal (MSMPR) crystallizers and tubular or plug flow crystallizers (PFC): laminarflow tubular crystallizers (LFTC), coiled flow inverter (CFI) crystallizers, segmented/slug flow crystallizers, and continuous oscillatory baffled crystallizers (COBC).

Compared with batch crystallization, advantages of continuous crystallization include:

constant flow rates of fresh aqueous mother liquor (feed syrup) and heating steam;

constant output of magma and crystallization vapor;

lower temperature difference between heating steam and magma possible;

easier process control, fixed set-point control;

easy execution of a balance simulation;

high volume/time efficiency;

reduced space and building requirements;

crystallizer can be placed outside; and lower investment and operating costs.

Preferably, the continuous or semi-continuous operation of the process according to the invention may involve any one, a subset or all of the stages described above with regard to the batch process, i.e. (i) feed phase, (ii) concentration phase, (iii) seeding point, (iv) crystal formation phase, (v) crystal growth phase, (vi) tightening phase, and (vii) discharge phase. However, in continuous or semi-continuous operation of the process according to the invention, these stages take place simultaneously, but spatially separated, in a continuous evaporating crystallizer. Again, a skilled person recognizes that modifications are possible, which are also contemplated.

Whereas in the batch process, all crystals ideally have an equally long retention time in the batch evaporating crystallizer, in continuous evaporating crystallization there typically is a retention time distribution for the individual allulose crystals. This has consequences for the spread of the resulting crystal size distribution for the individual allulose crystals. According to the invention, this effect is preferably countered by a larger addition of seed magma and/or a higher number of crystallization stages.

Preferably, under continuous or semi-continuous operation, the process according to the invention is operated under steady state conditions with respect to inflow and outflow of material. Preferably, under continuous or semi-continuous operation, solvent, supernatant and/or precipitate is continuously or semi-continuously withdrawn from the evaporating crystallizer by evaporation. Preferably, under continuous or semi-continuous operation, withdrawn solvent and/or supernatant and/or precipitate is substituted by fresh aqueous mother liquor that is supplied to the evaporating crystallizer.

Preferably, solvent is withdrawn from the evaporating crystallizer with a evaporation rate of at least 5.0 g/h, or at least 7.0 g/h, or at least 9.0 g/h, or at least 11 g/h, or at least 13 g/h, or at least 15 g/h, or at least 17 g/h.

Preferably, solvent is withdrawn from the evaporating crystallizer with a evaporation rate of at most 50 g/h, at most 48 g/h, at most 46 g/h, at most 44 g/h, at most 42 g/h, at most 40 g/h, at most 38 g/h, at most 36 g/h, at most 34 g/h, at most 32 g/h, or at most 30 g/h, or at most 28 g/h, or at most 26 g/h, or at most 24 g/h, or at most 22 g/h, or at most 20 g/h.

Preferably, solvent is withdrawn from the evaporating crystallizer with a evaporation rate within the range of 11±2.0 g/h, or 13±4.0 g/h, or 13±2.0 g/h, 15±6.0 g/h, or 15±4.0 g/h, or 15±2.0 g/h, or 17±8.0 g/h, 17±6.0 g/h, or 17±4.0 g/h, or 17±2.0 g/h, or 19±10 g/h, or 19±8.0 g/h, 19±6.0 g/h, or 19±4.0 g/h, or 19±2.0 g/h.

Preferably, the supply of fresh aqueous mother liquor to the evaporating crystallizer is controlled.

Preferably, under continuous or semi-continuous operation, the supply of fresh aqueous mother liquor to the evaporating crystallizer is regulated.

The supply of fresh aqueous mother liquor to the evaporating crystallizer is preferably regulated based upon measuring supersaturation and/or crystal content. According to the invention, suitable parameters that can be measured in order to determine or at least draw conclusions with respect to supersaturation and/or crystal content include but are not limited to (i) electrical conductivity;

(ii) boiling point elevation;

(iii) radio frequency;

(iv) refractive index;

(v) radiometric density;

(vi) microwaves (for measuring e.g. density, concentration, water content);

(vii) viscosity;

(viii) on-line crystal size observation and measurement (e.g. based upon Fraunhofer diffraction or back scattering);

(ix) ultrasonic absorption; and (x) ultrasonic velocity.

In preferred embodiments, any of the above parameters of the aqueous mother liquor within the evaporating crystallizer is measured and the supply of fresh aqueous mother liquor to the evaporating crystallizer is regulated according to the measured parameter to keep the measured parameter of the aqueous mother liquor within the evaporating crystallizer essentially constant or within the desired range.

In a preferred embodiment, the viscosity of the aqueous mother liquor within the evaporating crystallizer is measured and wherein the supply of fresh aqueous mother liquor to the evaporating crystallizer is regulated according to the measured viscosity to keep the viscosity of the aqueous mother liquor within the evaporating crystallizer essentially constant.

In another preferred embodiment, the density of the aqueous mother liquor within the evaporating crystallizer is measured and wherein the supply of fresh aqueous mother liquor to the evaporating crystallizer is regulated according to the measured density to keep the density of the aqueous mother liquor within the evaporating crystallizer essentially constant.

In still another preferred embodiment, the dry substance mass (dry substance content) of the aqueous mother liquor within the evaporating crystallizer is measured and wherein the supply of fresh aqueous mother liquor to the evaporating crystallizer is regulated according to the measured dry substance mass to keep the dry substance mass of the aqueous mother liquor within the evaporating crystallizer essentially constant.

In a further preferred embodiment, the particle size of the precipitate that is withdrawn from the evaporating crystallizer is measured and wherein the supply of fresh aqueous mother liquor to the evaporating crystallizer is regulated according to the measured particle size to keep the particle size of the precipitate essentially constant.

In particular, when a relative increase of fine particles is observed, fresh aqueous mother liquor is preferably supplied to the evaporating crystallizer and added to the aqueous mother liquor that is being processed therein. The diluting effect causes reduction of density and reduction of viscosity. In consequence, intermixing is improved. Crystal growth on existing crystallites is favored compared to spontaneous formation of new crystallites thereby leading to relative increase of coarse particles finally compensating the initial increase of fine particles.

In a preferred embodiment, the aqueous mother liquor is stirred with a stirrer within the evaporating crystallizer and the torque is measured at the stirrer, and wherein the supply of fresh aqueous mother liquor to the evaporating crystallizer is regulated according to the measured torque to keep the torque at the stirrer essentially constant.

In a preferred embodiment, the crystallization pressure is kept essentially constant over time, preferably until the end of crystallization, and wherein the crystallization temperature is regulated to keep the evaporation rate essentially constant.

In another preferred embodiment, the crystallization temperature is kept essentially constant over time, preferably until the end of crystallization, and wherein the crystallization pressure is regulated to keep the evaporation rate essentially constant.

In still another preferred embodiment, withdrawn solvent and/or supernatant and/or precipitate is substituted by fresh aqueous mother liquor that is supplied to the evaporating crystallizer; wherein the supply of fresh aqueous mother liquor to the evaporating crystallizer is regulated; and wherein the evaporation rate is determined and wherein the supply of fresh aqueous mother liquor to the evaporating crystallizer is regulated according to the determined evaporation rate to keep the evaporation rate essentially constant.

In a preferred embodiment, the crystallization pressure is kept essentially constant over time, preferably until the end of crystallization, and wherein the crystallization temperature is regulated to keep the supersaturation coefficient y essentially constant.

In another preferred embodiment, the crystallization temperature is kept essentially constant over time, preferably until the end of crystallization, and wherein the crystallization pressure is regulated to keep the supersaturation coefficient y essentially constant.

In still another preferred embodiment, withdrawn solvent and/or supernatant and/or precipitate is substituted by fresh aqueous mother liquor that is supplied to the evaporating crystallizer; wherein the supply of fresh aqueous mother liquor to the evaporating crystallizer is regulated; and wherein the supersaturation coefficient y is determined and wherein the supply of fresh aqueous mother liquor to the evaporating crystallizer is regulated according to the determined supersaturation coefficient y to keep the supersaturation coefficient y essentially constant.

The process according to the present invention may comprise one or more additional steps wherein the allulose crystals present in a massecuite, i.e. precipitate in supernatant, following separation from the mother liquor portion of the massecuite by centrifugation, filtration, decantation, membrane separation or other such physical separation method, are subjected to further processing.

Preferably, the process according to the invention comprises the additional step of (e) separating at least a portion of the precipitate from at least a portion of the supernatant.

Preferably, step (e) of the process according to the invention involves centrifugation.

For example, allulose crystals as separated from a mother liquor typically have some amount of the mother liquor on the outer surface to the crystals. Because the mother liquor generally contains some amount of impurities (substances other than allulose), the purity of the recovered crystals may be improved by subjecting the separated allulose crystals to one or more washing steps, wherein one or more volumes of a suitable liquid are used to wash the crystals. The washing step(s) may be performed in any suitable manner using techniques known in the art, such as passing the washing liquid through a bed of the allulose crystals or by slurrying the separated allulose crystals in a volume of the washing liquid and then subjecting the slurry to a physical separation step such as centrifugation, decantation, membrane separation and/or filtration to recover washed allulose crystals from the washing liquid.

Any suitable washing liquid may be utilized, such as water, an organic solvent (e.g., an alcohol, such as ethanol), a blend of water and one or more organic solvents, a blend of two or more organic solvents, and/or an aqueous solution comprised of at least one carbohydrate such as allulose. In one embodiment, the allulose crystals are washed with an allulose syrup or even a recovered mother liquor having a purity (with respect to allulose) that is higher than the purity of the residual mother liquor initially present in the crystals to be washed.

The purity of allulose can be determined by conventional methods that are known to the skilled person. Preferably, the purity of allulose is determined by HPLC, e.g. in accordance with Kunta Ravindhranath, Int. J. Res. Pharm. Sci., 2020, 11(1), 775-780.

Preferably, the process according to the invention comprises the additional step of (f) drying the solid allulose material.

The drying step may, for example, be carried out subsequent to a washing step or series of washing steps. The drying of the crystals may be performed in a fluidized bed dryer, a rotary dryer, a vacuum dryer or other such apparatus. For example, in the drying step, the allulose crystals may be dried using an air temperature of up to approximately 100° C., preferably no greater than 80° C., over a period of about 20 minutes to about 24 hours, more preferably about 20 minutes to about 6 hours.

Preferably, the solid allulose material comprises crystalline allulose optionally together with amorphous allulose.

Preferably, the solid allulose material has a degree of crystallinity of at least 90%; preferably at least 95%; more preferably at least 98%. The degree of crystallinity is preferably determined by x-ray diffraction comparing signals against a series of samples having a known degree on crystallinity.

Preferably, the solid allulose material essentially consists of crystalline allulose.

Preferably, the solid allulose material consists of particles having an average particle size d50 ($X_{Fe\ max}$) of at least 120 μm; preferably at least 140 μm; more preferably at least 160 μm; still more preferably at least 180 μm; yet more preferably at least 200 μm; most preferably at least 220 μm.

Preferably, the solid allulose material consists of particles having an average particle size d50 ($X_{Fe\ max}$) of at most 330 μm; preferably at most 310 μm; more preferably at most 290 μm; still more preferably at most 270 μm; yet more preferably at most 250 μm; most preferably at most 230 μm.

Preferably, the solid allulose material consists of particles having an average particle size d50 ($X_{Fe\ max}$) within the range of 75 to 500 μm, preferably 100 to 400 μm, more preferably 200 to 300 μm.

Preferably, particle size and particle size distribution are measured by image analysis, e.g. dynamic picture analysis using a Retsch Camsizer. Preferably, the crystalline allulose may comprise single crystals as well as agglomerates of crystals. When determining particle size and particle size distribution, agglomerates are treated like single crystals.

Preferably, particle size is determined by image analysis on the basis of the longest of all measured Feret diameters $X_{Fe\ max}$ and average particle size is expressed as the corresponding d50 value. Preferably, particle size is measured at 20 kPa in order to reduce agglomerates and conglomerates and in order to hardly damage crystals. Alternatively, particle size and average particle size (d50) are determined by means of a coulter counter, laser diffraction, or by sieve analysis in accordance with ICUMSA Method GS2/9-37.

Preferably, the solid allulose material has a residual content of alcohol of at most 5 ppm; preferably at most 2 ppm.

Another aspect of the invention relates to a solid allulose material obtainable or obtained by a process according to the invention as described above.

The following examples further illustrate the invention but are not to be construed as limiting its scope.

Comparative Example 1—Cooling Crystallization 5000 g of an allulose syrup having a dry substance mass (ds) of 70 wt.-% was concentrated in a rotary evaporator at 50 mbar and 60° C. to a ds of 83.8 wt.-%. The concentrated syrup was transferred into a cooling crystallizer and a slurry containing 0.1 wt.-% of undissolved allulose crystals was added while agitating the mixture at 55° C. under ambient pressure. Starting from 55° C., the suspension was cooled to 40° C. under varying cooling rates within about 80 hours.

The suspension was subjected to centrifugation and 1365 g (yield: 39 wt.-%) of allulose crystals were obtained. The particle size (d50, $X_{Fe\ max}$) of the allulose crystals was 148 μm (measured at 5 kPa using a Retsch Camsizer).

Inventive Example 1—Seeding in Isopropanol

An allulose syrup having a dry substance mass (ds) of 70 wt.-% was concentrated in a rotary evaporator at 50 mbar and 60° C. to a ds of 80.4 wt.-%. To 13560 g of the syrup, a slurry containing 0.02 wt.-% of undissolved crystalline allulose was added while agitating the mixture at 45° C. The pressure was reduced to 100 mbar. While further reducing the pressure, water was evaporated maintaining a constant evaporation rate within about 52 hours.

The resulting suspension was subjected to centrifugation and 4394 g (yield: 40 wt.-%) of allulose crystals were obtained. The particle size (d50, $X_{Fe\ max}$) of the allulose crystals was 212 μm (measured at 20 kPa using a Retsch Camsizer).

Inventive Example 2—Seeding in Syrup

An allulose syrup having a dry substance mass (ds) of 70 wt.-% was concentrated in a rotary evaporator at 50 mbar and 60° C. to a ds of 79.3 wt.-%. To 13884 g of the syrup, a slurry containing 0.02 wt.-% of undissolved crystalline allulose and 80 wt.-% of iso-propanol was added while agitating the mixture at 45° C. The pressure was reduced to 100 mbar. While further reducing the pressure, the solvents were evaporated (iso-propanol first followed by water) maintaining a constant evaporation rate within about 50 hours.

The resulting suspension was subjected to centrifugation and 4624 g (yield: 42 wt.-%) of allulose crystals were obtained. The particle size (d50, $X_{Fe\ max}$) of the allulose crystals was 226 μm (measured at 20 kPa using a Retsch Camsizer).

The experimental results are also compiled in the following table:

|  | Comparative Example | Inventive Example 1 | Inventive Example 2 |
| --- | --- | --- | --- |
| time | 80 hours | 52 hours | 50 hours |
| yield | 39 wt.-% | 40 wt.-% | 42 wt.-% |
| d50 | 148 μm | 212 μm | 226 μm |

Inventive Example 3—Cooling Crystallization a) General Methods

The following devices were used:
rotary evaporator Rotavapor R-220 SE, Co. Buchi;
evaporating crystallizer LF200, Co. Lenz (15 L);
2 KW thermostat from CC-K6s, Co. Huber;
Refractometer Pure S, Co. Schmidt und Haensch;
Heidolph Hei-Torque 200, Co. Heidolph Instruments;
allulose syrup L3121034, Co. Savanna Ingredients;
Vacuum pump CVC 3000; PC3001, Co. Vacuubrand; and
Laboratory centrifuge, Co. Hermle.

Refractometric index/refractive index was determined at 20° C. from the undiluted syrup using a refractometer (Pure S, Co. Schmidt und Haensch). Based upon calibration information of allulose compositions having a known allulose concentration, the weight content of allulose, i.e. the allulose concentration in the samples, was determined. Brix values were calculated from the measured values of the refractometric index/refractive index (i.e. also at 20° C.).

b) Experimental Design

For comparing the performance of the evaporating crystallization according to the invention (elevated temperature and reduced pressure) with a conventional cooling crystallization (reduced temperature and atmospheric pressure), the amount of water to be evaporated in evaporating crystallization should be comparable to the change in solubility due to the cooling rate in cooling crystallization.

With regard to evaporating crystallization, based upon the saturation point, the theoretical Brix values of the allulose syrup
    at the inoculation temperature (43.4° C.),
    at a temperature 0.1° C. below the inoculation temperature (43.2° C.),
    at a temperature 0.2° C. below the inoculation temperature (43.2° C.), and
    at a temperature 0.3° C. below the inoculation temperature (43.1° C.) were calculated.

Using the thus obtained Brix values, the corresponding changes of the Brix values in conventional cooling crystallization at cooling rates of 0.1° C./h, 0.2° C./h and 0.3° C./h were determined. For simplicity, the change of the Brix values was assumed to be a percentage of the change in dry matter. The calculated, i.e. theoretical Brix values (at saturation, purity: 90.2%) at the corresponding temperatures after maintaining the set temperature for 1 h are summarized in the table here below; the cooling rates indicate the corresponding conditions in cooling crystallization:

| Cooling rate | Temperature | Brix [wt.-%] | Δ Brix [%] |
|---|---|---|---|
| 0° C./h | 43.4° C. | 79.42 | — |
| 0.1° C./h | 43.3° C. | 79.38 | 0.037 |
| 0.2° C./h | 43.2° C. | 79.34 | 0.077 |
| 0.3° C./h | 43.1° C. | 79.30 | 0.117 |

When subjecting 14.5 kg of an allulose syrup (Brix 80.26) to an evaporating crystallization according to the invention, the following evaporation rates must be met in order to be equivalent to a corresponding cooling crystallization at different cooling rates:

| Cooling rate | Evaporation rate |
|---|---|
| 0.1° C./h | 5.8 g/h |
| 0.2° C./h | 11.6 g/h |
| 0.3° C./h | 17.4 g/h | c) Preparation of Starting Material for Evaporating Crystallization 19.8 kg of allulose syrup were concentrated to approx. 80 Brix in a rotary evaporator at 60° C. and 60 mbar. A total of 14.5 kg of concentrated allulose syrup was transferred to the crystallizer and stirred at 50° C. and at 80 rpm overnight. To the allulose syrup, 2 g of crystalline allulose with a d50 of 12 μm was added while agitating the mixture at 43.4° C. The pressure was reduced to 50 mbar.

Values of RI, Brix, and allulose content of the allulose syrup were measured prior to inoculation and ds, density, purity, corresponding saturation temperature and inoculation temperature at supersaturation of 1.01 were calculated:

| Brix [%] | 80.26 |
|---|---|
| RI | 1.49143 |
| allulose content [g/L] | 1107.02 |
| ds [%] | 86.22 |
| density [kg/L] | 1.4234 |
| allulose content [g/kg] | 777.74 |
| purity [%] | 90.2 |
| saturation temperature [° C.] | 45.4 |
| inoculation temperature [° C.] | 43.4 |
| supersaturation | 1.01 |

Calculation of the saturation temperature was carried out according to Eq. 1:

$$T_{saturation} = -196.277317 + 0.45862802 * purity[\%] + Brix[\%] * 2.49673802 \qquad \text{Eq. 1}$$

Calculation of the inoculation temperature at a supersaturation of 1.01 was carried out according to Eq. 2:

$$T_{inoculation} = \frac{\dfrac{Brix\ [\%]}{1.01} - 78.7434553 + 0.18382655 * purity\ [\%]}{0.39769988} \qquad \text{Eq. 2}$$

d) Evaporating Crystallization

Evaporating crystallization was performed in two stages:

first stage: batch process second stage: fed-batch process (semi-continuous)

During the first stage of the evaporating crystallization, the pressure was changed after certain time intervals and maintained in the range of from 40 to 50 mbar. The allulose syrup was examined microscopically and values of RI, Brix and the weight of the evaporated water were determined after each pressure change. At the end of the first stage, a fraction of the resulting magma was centrifuged (without washing) and the crystal content was determined. The values of RI and Brix of the magma and effluent were determined. Then, the magma was left tempered and stirred without vacuum for two days.

During the second stage of the evaporating crystallization, more concentrated allulose syrup with a Brix of 81.47 (RI: 1.49456) was added to the crystallizer as a post-pull (fed-batch). The pressure was reduced to 44 mbar and the allulose syrup was examined as described above. At the end of the second stage, a fraction of the resulting magma was centrifuged (without washing) and the crystal content was determined. The values of RI and Brix of the magma and effluent were determined.

Based on the temperature and the Brix measurement, the existing supersaturation could be calculated for the time of sampling according to Eq. 3 assuming that the purity remained unchanged at 90.2% during crystallization.

$$supersaturation = \frac{Brix}{78.74 + 0.39 * T - 0.18 * purity} \qquad \text{Eq. 3}$$

e) Results

The results are listed in the table here below:

| | time after inoculation | pressure | Σ evaporated water | water evaporation rate | magma/effluent | | super-saturation | centrifugation weight | |
|---|---|---|---|---|---|---|---|---|---|
| | | | | | Brix | RI | | in | out |
| | [h] | [mbar] | [g] | [g/h] | | | | | |
| 1st | 0 | 1000 | 0 | | 80.26 | 1.49143 | 1.011 | n.d. | n.d. |
| stage | 1.5 | 50 | 0 | | n.d. | n.d. | n.d. | n.d. | n.d. |
| | 21 | 40 | 44 | 2.3 | 80.73 | 1.49256 | 1.016 | n.d. | n.d. |
| | 25 | 45 | 237 | 48.1 | 81.82 | 1.49548 | 1.030 | n.d. | n.d. |
| | 50.5 | 43 | 464 | 8.9 | 81.32 | 1.49418 | 1.024 | n.d. | n.d. |
| | 67.25 | 44 | 818 | 21.5 | 81.38 | 1.49433 | 1.025 | n.d. | n.d. |

-continued

| | time after inoculation | pressure | Σ evaporated water | water evaporation rate | magma/effluent | | super- saturation | centrifugation weight | |
|---|---|---|---|---|---|---|---|---|---|
| | | | | | Brix | RI | | in | out |
| | [h] | [mbar] | [g] | [g/h] | | | | | |
| | 71.5 | 1000 | 920 | 22.7 | 80.62/81.67 | 1.49231/1.49504 | 1.015 | 283 | 128 (45%) |
| | 141.5 | 1000 | 920 | n.d. | 79.40 | 1.48912 | 0.999 | n.d. | n.d. |
| 2nd | | | | adding allulose syrup (fed-batch) | | | | | |
| | 144.75 | 44 | n.d. | n.d. | 79.73 | 1.48997 | n.d. | n.d. | n.d. |
| | 163.75 | 1000 | 1270 | 18.4 | 81.38/80.86 | 1.49433/1.49292 | 1.025 | 385 | 216 (56%) |

After the first stage of crystallization (batch), a crystal content of 45 wt.-% could be determined. After adding more allulose syrup to the crystallizer in the second stage of crystallization (fed-batch), a crystal content of 56 wt.-% could be determined.

Figure 2:
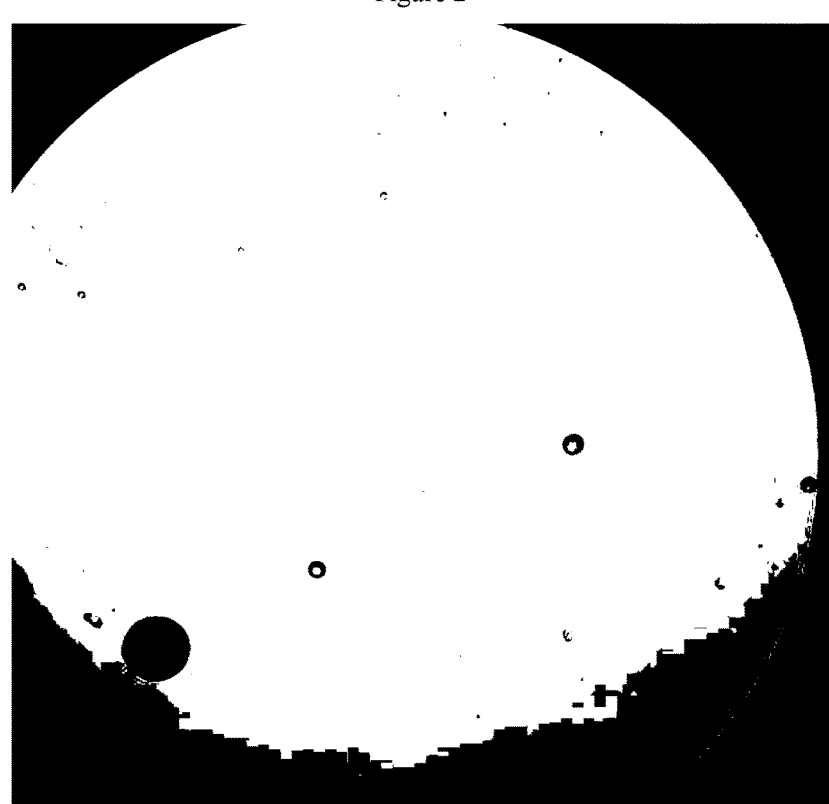
FIGS. 2 to 5 show microscopic images of allulose syrup at inoculation temperature at various time points after inoculation.
Figure 3:
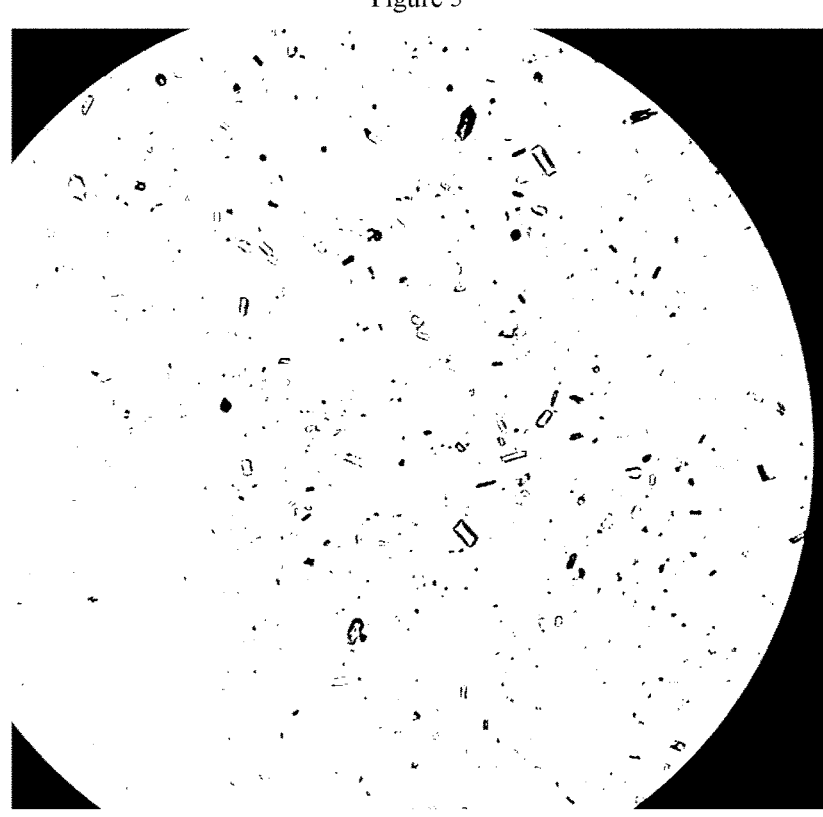
Figure 4:
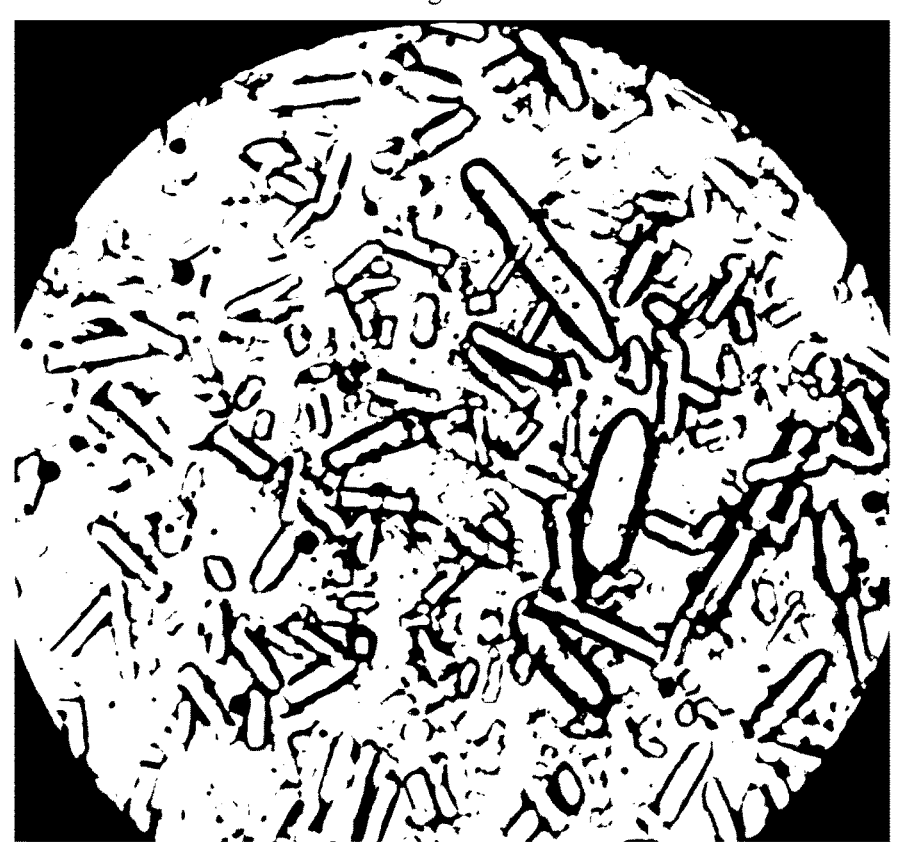
Figure 5:
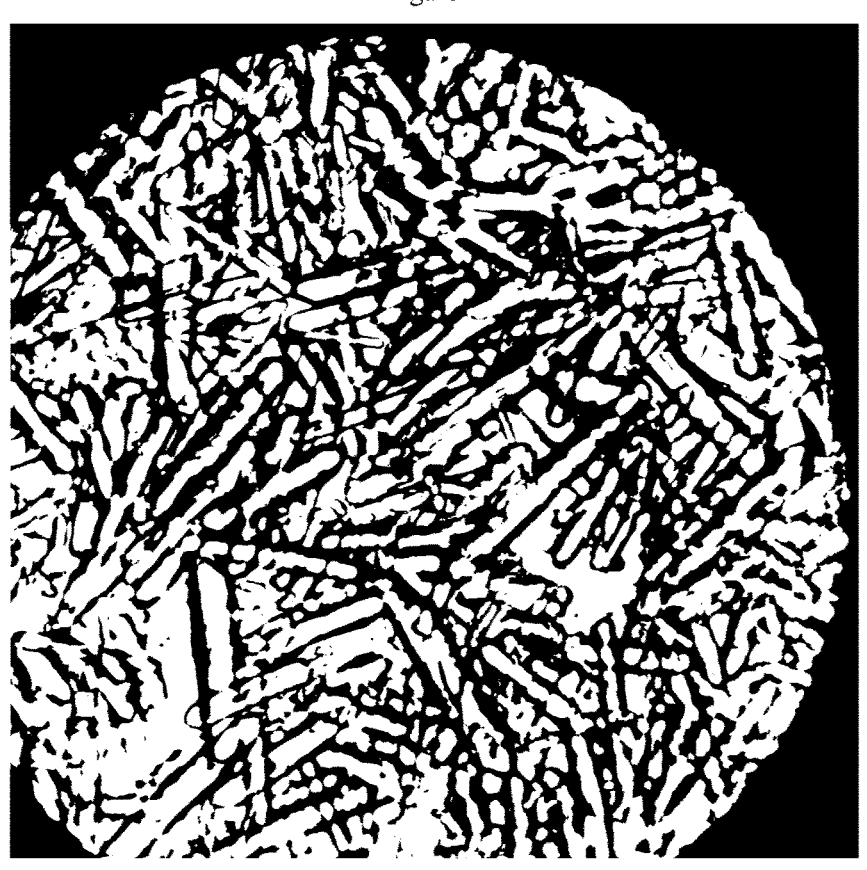
Figure 6:
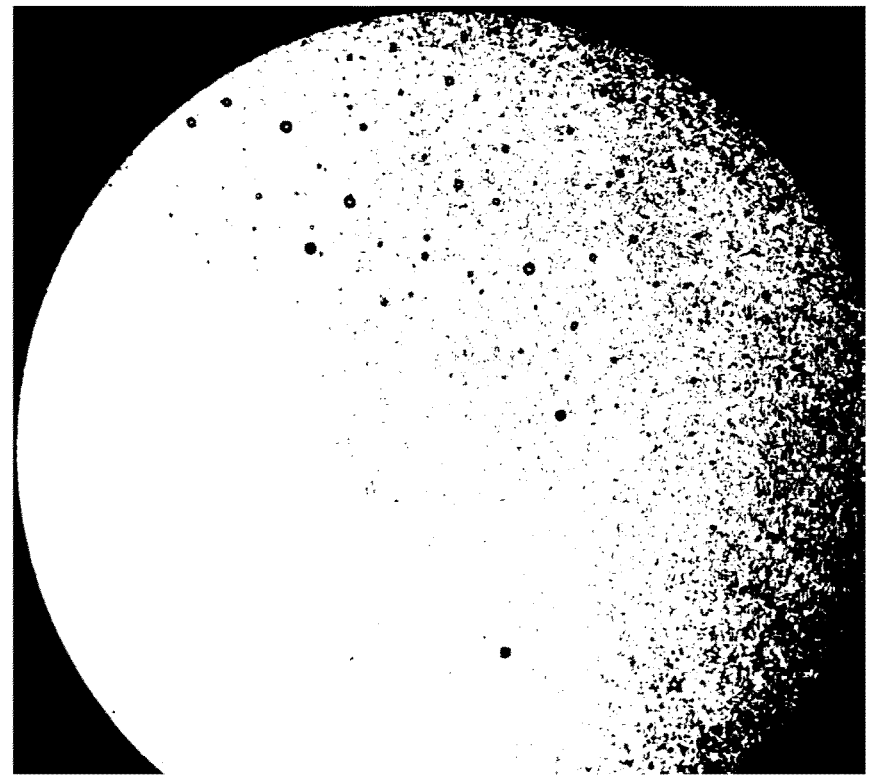
FIG. 6 shows a microscopic image of allulose syrup after centrifugation.
Figure 7:
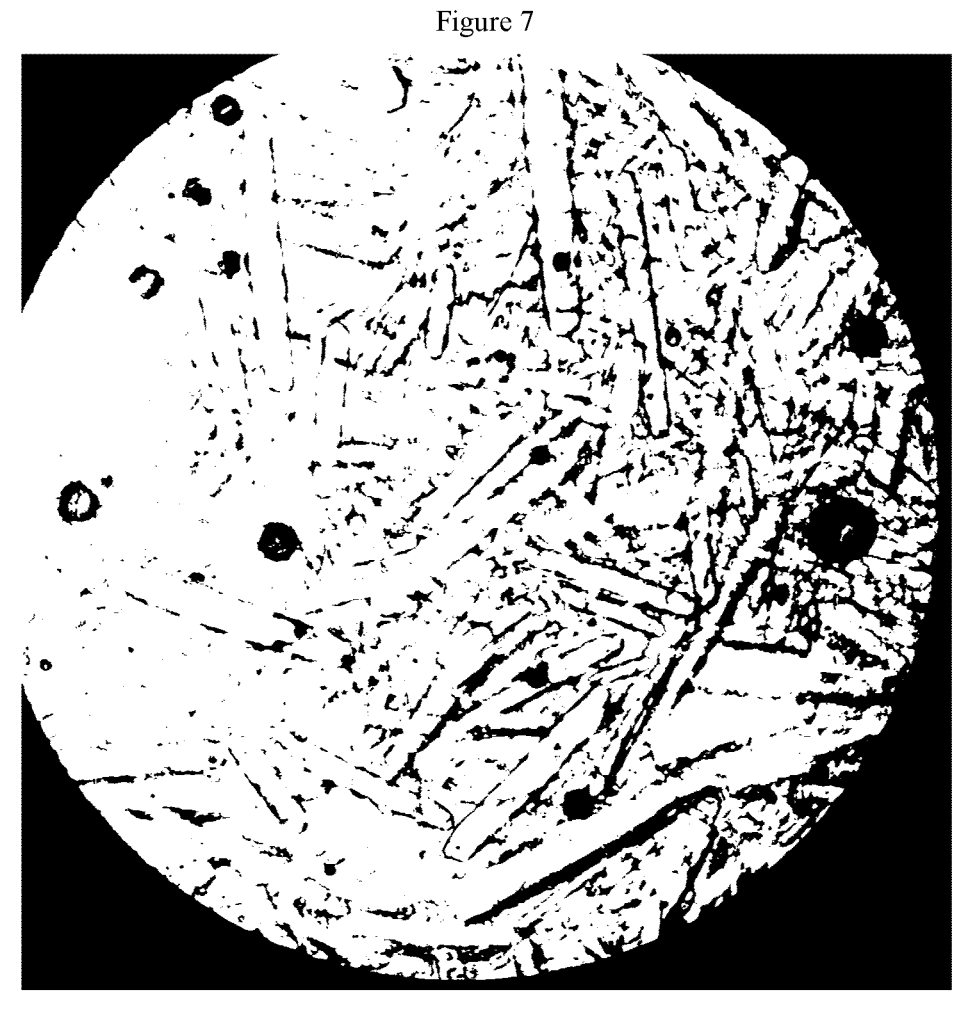
FIG. 7 shows a microscopic image of allulose syrup after crystallization with redraw.

FIGS. 1 to 7 show microscopic images of allulose syrup before vacuum crystallization (FIG. 1), and during or after vacuum crystallization after inoculation (FIG. 2 after 1.5 h, FIG. 3 after 21 h, FIG. 4 after 50.5 h. FIG. 5 after 67 h, FIG. 6 after centrifugation, FIG. 7 after crystallization with redraw).

Figure 8:
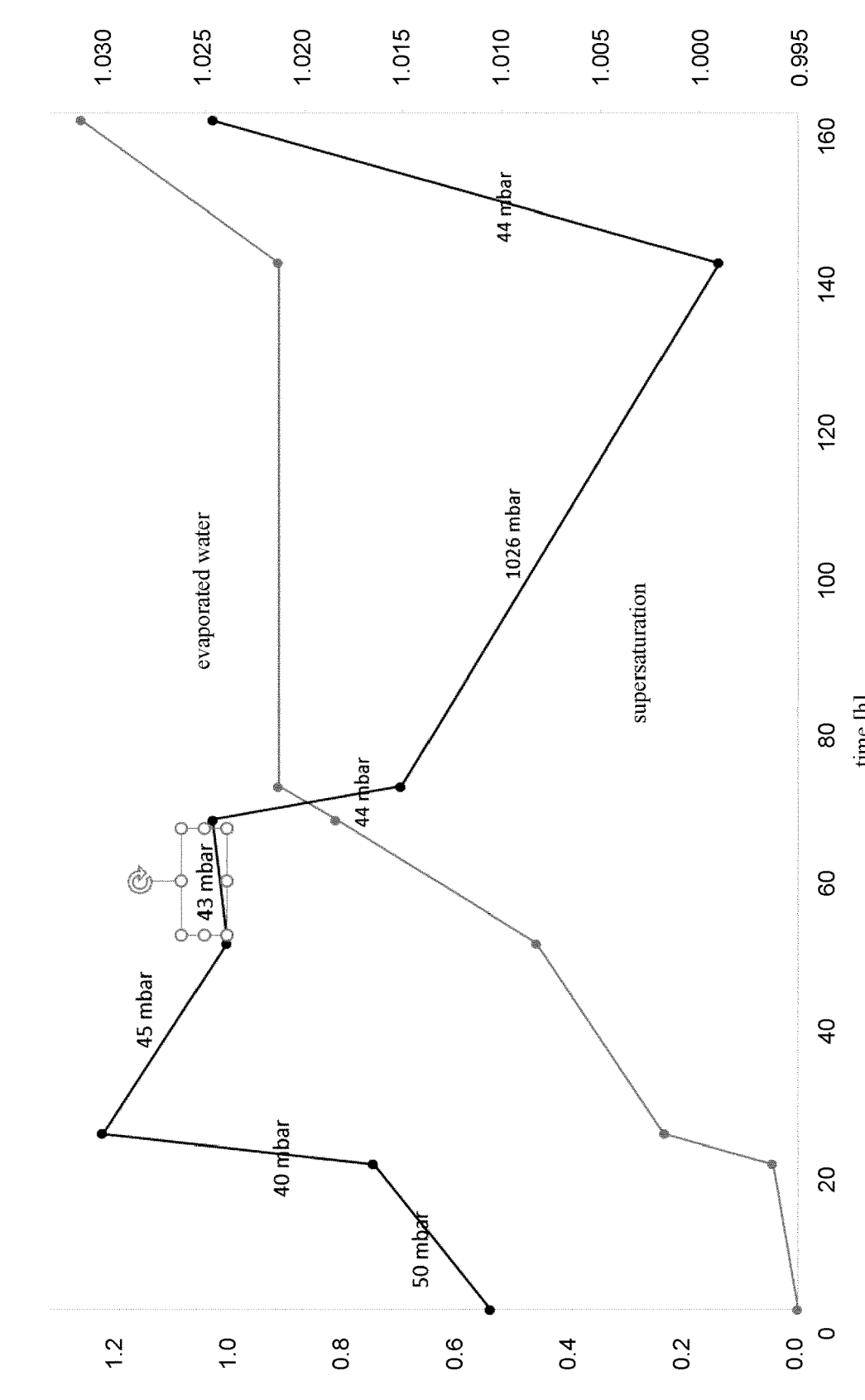
FIG. 8 shows a plot of supersaturation and amount of evaporated water as a function of time at 43.4° C. and different vacuum.

FIG. 8 shows a plot of calculated supersaturation and amount of evaporated water as a function of time at 43.4° C. and different vacuum. The increase in the amount of evaporated water can be seen at different vacuum levels between 40 and 50 mbar. It can also be seen that in the course of evaporating crystallization, the supersaturation initially increased and then decreased again.

The above experimental data demonstrate that evaporating crystallization with a vacuum between 40 and 50 mbar is feasible and that a temperature of the crystallization below 50° C. is reasonable. Furthermore, evaporating crystallization with post-pull, i.e. in fed-batch mode, is generally feasible.

What is claimed is:

1. A process for the preparation of a solid allulose material comprising crystalline allulose, the method comprising the steps of
(a) providing in an evaporating crystallizer an aqueous mother liquor containing dissolved allulose;
(b) maintaining until the end of crystallization the aqueous mother liquor within the evaporating crystallizer at a crystallization temperature within a range of from 20 to 55° C.;
(c) maintaining until the end of crystallization the vapor phase above the aqueous mother liquor within the evaporating crystallizer at a crystallization pressure within a range of from 40 to 200 mbar; and
(d) inducing crystallization of allulose from the aqueous mother liquor at the crystallization temperature and at the crystallization pressure in a supersaturated state thereby obtaining the solid allulose material as a precipitate, and a supernatant; wherein crystallization is induced at a supersaturation coefficient y of the aqueous mother liquor of at most 1.05, including reducing the crystallization pressure from a first crystallization pressure to a second crystallization pressure.

2. The process according to claim 1, wherein
the crystallization temperature is 29° C. to 55° C.; and/or 45+/−3° C.;
optionally wherein the crystallization temperature is kept essentially constant over time, until the end of crystallization; or does not change relatively by more than 2.0° C.

3. The process according to claim 1, wherein step (b) additionally includes maintain in the vapor phase above the aqueous mother liquor at a vapor temperature within the range of from 25 to 65° C.;
optionally, wherein the vapor phase above the aqueous mother liquor is does not change relatively by more than 2.0° C.; by not more than 1.5° C.; by not more than 1.0° C.; or by not more than 0.5°.

4. The process according to claim 1,
wherein the crystallization pressure is at least 41 mbar, or at least 42 mbar, or at least 43 mbar, or at least 44 mbar, or at least 45 mbar, or at least 46 mbar; optionally wherein the crystallization pressure is at least 60 mbar, or at least 61 mbar, or at least 62 mbar, or at least 63 mbar, or at least 64 mbar, or at least 65 mbar, or at least 66 mbar; and
wherein the crystallization pressure is at most 180 mbar, or at most 160 mbar, or at most 140 mbar, or at most 120 mbar, or at most 100 mbar, or at most 90 mbar, or at most 80 mbar, or at most 70 mbar, or at most 65 mbar, or at most 64 mbar, or at most 63 mbar, or at most 62 mbar, or at most 61 mbar, or at most 60 mbar;
optionally, wherein the crystallization pressure is within the range of from 45 to 200 mbar; or 46 to 200 mbar; or 40 to 100 mbar; or 45 to 100 mbar; or 46 to 100 mbar; or 40 to 60 mbar; or 45 to 60 mbar; or 46 to 60 mbar or; 60 to 200 mbar; or 61 to 200 mbar; or 62 to 200 mbar; or 60 to 100 mbar; or 61 to 100 mbar; or 62 to 100 mbar;
optionally wherein the crystallization pressure is kept essentially constant over time until the end of crystallization; and does not change relatively by more than 20 mbar; or by not more than 15 mbar; or by not more than 10 mbar; or by not more than 5 mbar.

5. The process according to claim 1, wherein in step (d) crystallization is induced by means of seed crystals;
optionally wherein the seed crystals are added to the aqueous mother liquor that is contained in the evaporating crystallizer.

6. The process according to claim 5, wherein the number of crystals of crystalline allulose that are obtained is at most 150% of the number of seed crystals that are employed.

7. The process according to claim 5,
wherein the seed crystals are added to the aqueous mother liquor before it is supplied to the evaporating crystallizer; or
optionally wherein the seed crystals are provided in form of a suspension in an alcoholic liquid, which is added to the aqueous mother liquor, optionally wherein the alcoholic liquid comprises methanol, ethanol, n-propanol, iso-propanol, tert-butanol or any combination thereof.

8. The process according to claim 5, wherein the seed crystals are provided in form of a suspension in an alcoholic liquid, which is added to the aqueous mother liquor, wherein the volume of the suspension is at most 1.0 vol.-% of the volume of the aqueous mother liquor that is contained in the evaporating crystallizer.

9. The process according to claim 1, wherein in step (d) crystallization of allulose from the aqueous mother liquor is induced at the crystallization temperature and at the crystallization pressure in a metastable zone of the supersaturated state.

10. The process according to claim 1, wherein in step (d) of the process according to the invention crystallization is induced at a supersaturation coefficient y of the aqueous mother liquor of at least 1.01, or at least 1.02, or at least 1.03, or at least 1.04:

optionally wherein in step (d) crystallization of allulose from the aqueous mother liquor is induced at the crystallization temperature and at the crystallization pressure in an intermediate zone of the supersaturated state or wherein in step (d) crystallization of allulose from the aqueous mother liquor is induced at the crystallization temperature and at the crystallization pressure in a labile zone of a supersaturated state.

11. The process according to claim 1, wherein in step (d) of the process according to the invention crystallization is induced at a supersaturation coefficient y of the aqueous mother liquor of at most 1.04, or at most 1.03, or at most 1.02, or at most 1.01, optionally wherein the supersaturated state is achieved by increasing the allulose concentration as a consequence of evaporation under reduced pressure.

12. The process according to claim 1, wherein step (d) comprises adding a suspension of seed crystals in an aqueous non-alcoholic liquid to the aqueous mother liquor;

maintaining the vapor phase above the aqueous mother liquor within the evaporating crystallizer at the crystallization pressure until the end of crystallization; wherein the crystallization pressure is kept essentially constant over time, and does not change relatively by more than 20 mbar; and/or wherein step (d) comprises the substeps of (d-1) evaporating water from the aqueous mother liquor thereby increasing the concentration of dissolved allulose until spontaneous crystallization occurs and/ or inducing crystallization by means of seed crystals;

(d-2) promoting crystal growth by adding further aqueous mother liquor; and (d-3) withdrawing precipitate from the evaporating crystallizer, optionally wherein the crystallization temperature at all substeps is kept essentially constant over time until the end of crystallization; and/or wherein the aqueous mother liquor provided in step (a) has a content of dry matter of at least 80 wt.-%; relative to the total weight of the aqueous mother liquor; and/or wherein the aqueous mother liquor provided in step (a) has an allulose content of at least 90 wt.-%; relative to the total content of dry matter that is contained in the aqueous mother liquor; and/or wherein the aqueous mother liquor provided in step (a) has a fructose content of at most 10 wt; relative to the total content of dry matter that is contained in the aqueous mother liquor.

13. The process according to claim 1, wherein the aqueous mother liquor provided in step (a) has a density within the range of from 1.36 to 1.46 g cm$^{-3}$.

14. The process according to claim 1, wherein the aqueous mother liquor provided in step (a) has a fructose content of at least 0.1 wt.-%;

relative to the total content of dry matter that is contained in the aqueous mother liquor and/or wherein the aqueous mother liquor provided in step (a) has a fructose content of at least 0.1 wt.-%;

relative to the total weight of the aqueous mother liquor optionally wherein the aqueous mother liquor provided in step (a) has a fructose content of at most 10 wt.-%;

relative to the total weight of the aqueous mother liquor;

optionally wherein the aqueous mother liquor provided in step (a) has a content of allulose of at least 80 wt.-%; relative to the total weight of the aqueous mother liquor.

15. The process according to claim 1, wherein the at least a portion of the supernatant is recycled to step (a);

optionally wherein the process comprises the additional step of (e) separating at least a portion of the precipitate from at least a portion of the supernatant, optionally wherein step (e) involves centrifugation.

16. The process according to claim 1, wherein the process is further characterized by one or any combinations of the following:

the supernatant obtained in step (d) has a content of dry matter of at most 78 wt.-%; relative to the total weight of the supernatant; and/or the process comprises the additional step of (e) separating at least a portion of the precipitate from at least a portion of the supernatant, optionally wherein step (e) involves centrifugation; and/or the process comprises the additional step of (f) drying the solid allulose material; and/or the aqueous mother liquor at the crystallization temperature has a viscosity of at most 2000 mPa-s measured by means of a rotary viscosimeter at a speed of 100 rpm; and/or the viscosity of the aqueous mother liquor within the evaporating crystallizer does not change relatively by more than 100 mPa-s; and/or the process is operated as a batch process, the process is operated as a semi-continuous process, the process is operated as a continuous process, or the process is operated as a fed-batch process; and/or a precipitate and/or a supernatant is continuously or semi-continuously withdrawn from the evaporating crystallizer; and/or withdrawn solvent and/or supernatant and/or precipitate is substituted by fresh aqueous mother liquor that is supplied to the evaporating crystallizer; and/or the process comprises the stages of: (i) at least partially filling the evaporating crystallizer with the aqueous mother liquor, (ii) performing evaporating crystallization, (iii) supplying fresh aqueous mother liquor to the evaporating crystallizer, (iv) performing evaporating crystallization, and (v) optionally, emptying of the evaporating crystallizer; optionally wherein at stage (iii) the fresh aqueous mother liquor is supplied to the evaporating crystallizer when a predetermined condition has been achieved in the course of stage (ii), wherein said predetermined condition is selected from the group consisting of a viscosity of the aqueous mother liquor within the evaporating crystallizer, a density of the aqueous mother liquor within the evaporating crystallizer, a dry substance mass of the aqueous mother liquor within the evaporating crystallizer, a particle size of the precipitate that is withdrawn from the evaporating crystallizer, a torque at a stirred stirring the aqueous mother liquor within the evaporating crystallizer, a volume of the aqueous mother liquor within the evaporating crystallizer, a yield of the precipitate that has been withdrawn from the evaporating crystallizer a volume or weight of water that has been evaporated and withdrawn from the evaporating crystallizer; an evaporation rate, a supersaturation coefficient y of the aqueous mother liquor within the evaporating crystallizer, a crystallization pressure, and a crystallization temperature; and/or the crystallization pressure is kept essentially constant over time until the end of crystallization and wherein the crystallization temperature is regulated to keep the evaporation rate essentially constant; and/or the crystallization temperature is kept essentially constant over time until the end of crystallization and wherein the crystallization pressure is regulated to keep the evaporation rate essentially constant; and/or the crystallization pressure is kept essentially constant over time until the end of crystallization and wherein the crystallization temperature is regulated to keep the supersaturation coefficient y essentially constant; and/or the crystallization temperature is kept essentially constant over time until the end of crystallization and wherein the crystallization pressure is regulated to keep the supersaturation coefficient y essentially constant; and/or withdrawn solvent and/or supernatant and/or precipitate is substituted by fresh aqueous mother liquor that is supplied to the evaporating crystallizer;

wherein the supply of fresh aqueous mother liquor to the evaporating crystallizer is regulated; and wherein the supersaturation coefficient y is determined and wherein the supply of fresh aqueous mother liquor to the evaporating crystallizer is regulated according to the determined supersaturation coefficient y to keep the supersaturation coefficient y essentially constant; and/or the process is free of any step of crystallization under atmospheric pressure; and/or the process is free of any step of cooling crystallization; and/or the solid allulose material comprises crystalline allulose optionally together with amorphous allulose; and/or the solid allulose material has a degree of crystallinity of at least 90%; and/or the solid allulose material consists essentially of crystalline allulose; and/or the solid allulose material consists of particles having an average particle size d50 ($X_{Fe\ max}$) of at least 120 μm; and/or the solid allulose material consists of particles having an average particle size d50 ($X_{Fe\ max}$) of at most 330 μm; and/or the solid allulose material consists of particles having an average particle size d50 ($X_{Fe\ max}$) within the range of 75 to 500 μm; and/or the solid allulose material has a residual content of alcohol of at most 5 ppm.

17. The process according to claim 1, wherein solvent is continuously or semi-continuously withdrawn from the evaporating crystallizer by evaporation;

wherein solvent is withdrawn from the evaporating crystallizer with an evaporation rate:

(i) of at least 5.0 g/h, or at least 7.0 g/h, or at least 9.0 g/h, or at least 11 g/h, or at least 13 g/h, or at least 15 g/h, or at least 17 g/h; and/or (ii) of at most 50 g/h, at most 48 g/h, at most 46 g/h, at most 44 g/h, at most 42 g/h, at most 40 g/h, at most 38 g/h, at most 36 g/h, at most 34 g/h, at most 32 g/h, or at most 30 g/h, or at most 28 g/h, or at most 26 g/h, or at most 24 g/h, or at most 22 g/h, or at most 20 g/h; and/or (iii) within the range of 11±2.0 g/h, or 13±4.0 g/h, or 13±2.0 g/h, 15±6.0 g/h, or 15±4.0 g/h, or 15±2.0 g/h, or 17±8.0 g/h, 17±6.0 g/h, or 17±4.0 g/h, or 17±2.0 g/h, or 19±10 g/h, or 19±8.0 g/h, 19±6.0 g/h, or 19±4.0 g/h, or 19±2.0 g/h;

optionally wherein the process is operated as a semi-continuous process, a continuous process, or a fed-batch process.

18. The process according to claim 1, wherein withdrawn solvent and/or supernatant and/or precipitate is substituted by fresh aqueous mother liquor that is supplied to the evaporating crystallizer;

wherein the supply of fresh aqueous mother liquor to the evaporating crystallizer is controlled or regulated;

optionally, wherein the viscosity of the aqueous mother liquor within the evaporating crystallizer is measured and wherein the supply of fresh aqueous mother liquor to the evaporating crystallizer is regulated according to the measured viscosity to keep the viscosity of the aqueous mother liquor within the evaporating crystallizer essentially constant;

optionally, wherein the density of the aqueous mother liquor within the evaporating crystallizer is measured and wherein the supply of fresh aqueous mother liquor to the evaporating crystallizer is regulated according to the measured density to keep the density of the aqueous mother liquor within the evaporating crystallizer essentially constant;

optionally, wherein the dry substance mass of the aqueous mother liquor within the evaporating crystallizer is measured and wherein the supply of fresh aqueous mother liquor to the evaporating crystallizer is regulated according to the measured dry substance mass to keep the dry substance mass of the aqueous mother liquor within the evaporating crystallizer essentially constant;

optionally, wherein the particle size of the precipitate that is withdrawn from the evaporating crystallizer is measured and wherein the supply of fresh aqueous mother liquor to the evaporating crystallizer is regulated according to the measured particle size to keep the particle size of the precipitate essentially constant;

optionally, wherein the aqueous mother liquor is stirred with a stirrer within the evaporating crystallizer and the torque is measured at the stirrer, and wherein the supply of fresh aqueous mother liquor to the evaporating crystallizer is regulated according to the measured torque to keep the torque at the stirrer essentially constant.

19. A solid allulose material obtainable or obtained by the process of claim 1, optionally, wherein the solid allulose material has a residual total amount of alcohol of at most 5 ppm.

20. The process of claim 1, wherein the first crystallization pressure is within a range of 50 to 200 mbar and the second crystallization pressure is within a range of 40 to 100 mbar; optionally wherein the first crystallization pressure is within the range of 80±20 mbar and the second crystalliza-
tion pressure is within the range of 50±10 mbar.

\* \* \* \* \*